(12) United States Patent
Okawa et al.

(10) Patent No.: US 8,385,617 B2
(45) Date of Patent: Feb. 26, 2013

(54) IMAGING DEVICE FOR DENTAL TREATMENT, AND INSTRUMENT UNIT FOR DENTAL TREATMENT WITH IMAGING DEVICE

(75) Inventors: Shinichi Okawa, Kyoto (JP); Seiichiro Yamashita, Kyoto (JP); Kazunari Matoba, Kyoto (JP)

(73) Assignee: J. Morita Manufacturing Corporation, Kyoto (JP)

( * ) Notice: Subject to any disclaimer, the term of this patent is extended or adjusted under 35 U.S.C. 154(b) by 191 days.

(21) Appl. No.: 12/736,520

(22) PCT Filed: Jun. 2, 2009

(86) PCT No.: PCT/JP2009/060046
§ 371 (c)(1),
(2), (4) Date: Oct. 14, 2010

(87) PCT Pub. No.: WO2009/148044
PCT Pub. Date: Dec. 10, 2009

(65) Prior Publication Data
US 2011/0058716 A1    Mar. 10, 2011

(30) Foreign Application Priority Data
Jun. 6, 2008 (JP) .................................. 2008-149577

(51) Int. Cl.
*G06K 9/00* (2006.01)
(52) U.S. Cl. ........................................................ 382/128

(58) Field of Classification Search .......... 382/128–134; 128/920–925; 356/39–49; 600/407–414, 600/424–426; 345/581–618
See application file for complete search history.

(56) References Cited

U.S. PATENT DOCUMENTS
2008/0017787 A1    1/2008   Okawa et al.

FOREIGN PATENT DOCUMENTS

| AT | 396 740 B | 11/1993 |
|---|---|---|
| JP | H4-503320 | 6/1992 |
| JP | H05-031125 | 2/1993 |
| JP | H5-337078 A | 12/1993 |
| JP | H10-66677 | 3/1998 |
| JP | 2004-154211 A | 6/2004 |
| JP | 2005-312727 A | 11/2005 |
| JP | 2006-6968 | 1/2006 |
| JP | 3126905 B | 11/2006 |
| JP | 3126905 (U) | 11/2006 |
| JP | 2007-143602 A | 6/2007 |
| WO | WO 2004/112638 A | 12/2004 |
| WO | WO 2005/104926 | 11/2005 |
| WO | WO 2007/002758 | 1/2007 |

*Primary Examiner* — Atiba O Fitzpatrick
(74) *Attorney, Agent, or Firm* — DLA Piper LLP (US)

(57) ABSTRACT

An imaging device for dental treatment for use in an instrument for dental treatment with a head to which a rotary cutting tool can be attached. The imaging device for dental treatment comprises: an imaging module with an imaging element; and a mounting section through which the imaging module is detachably attached to the instrument for dental treatment such that the imaging module is on the bottom side or on the lateral side of the head, and that the imaging module is in a posture that causes the imaging axis of the imaging module and the rotary axis of the rotary cutting tool to be substantially parallel.

19 Claims, 31 Drawing Sheets

F I G. 3
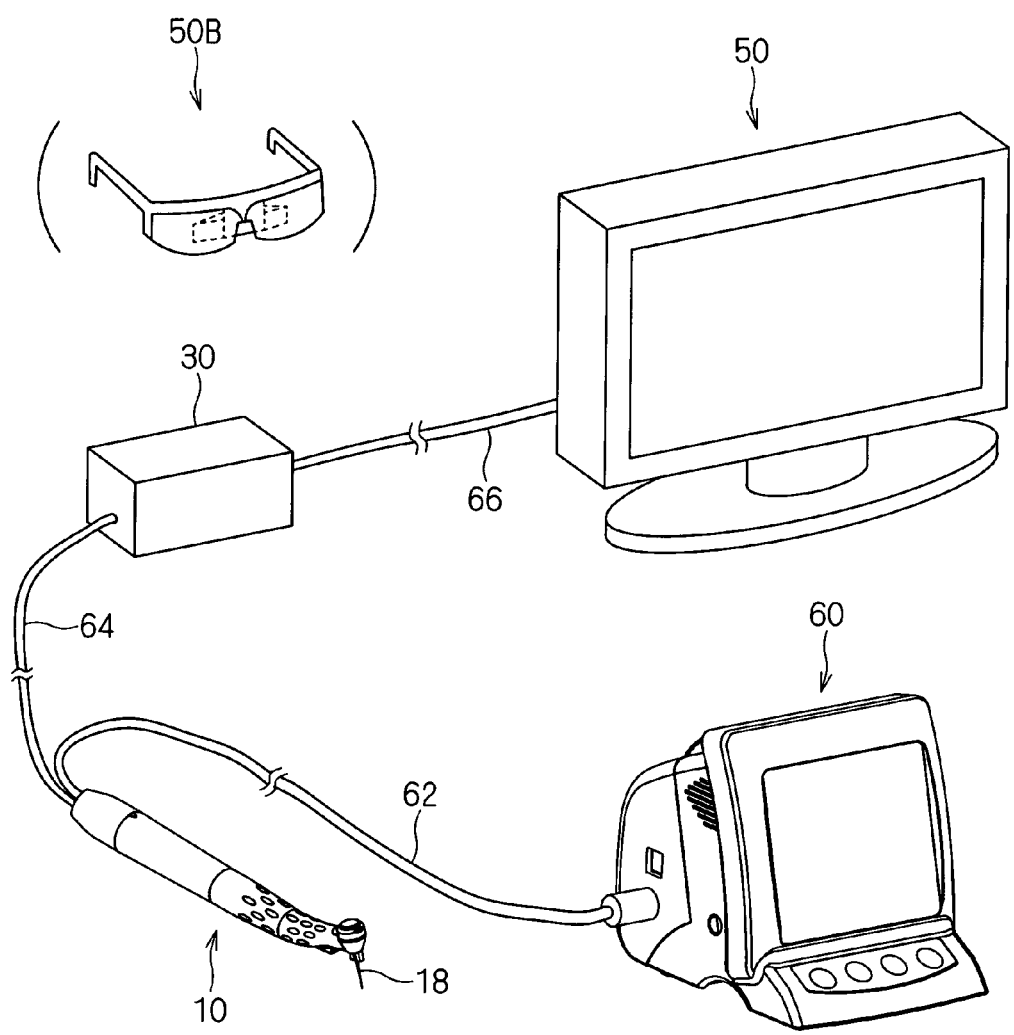

F I G . 3 2
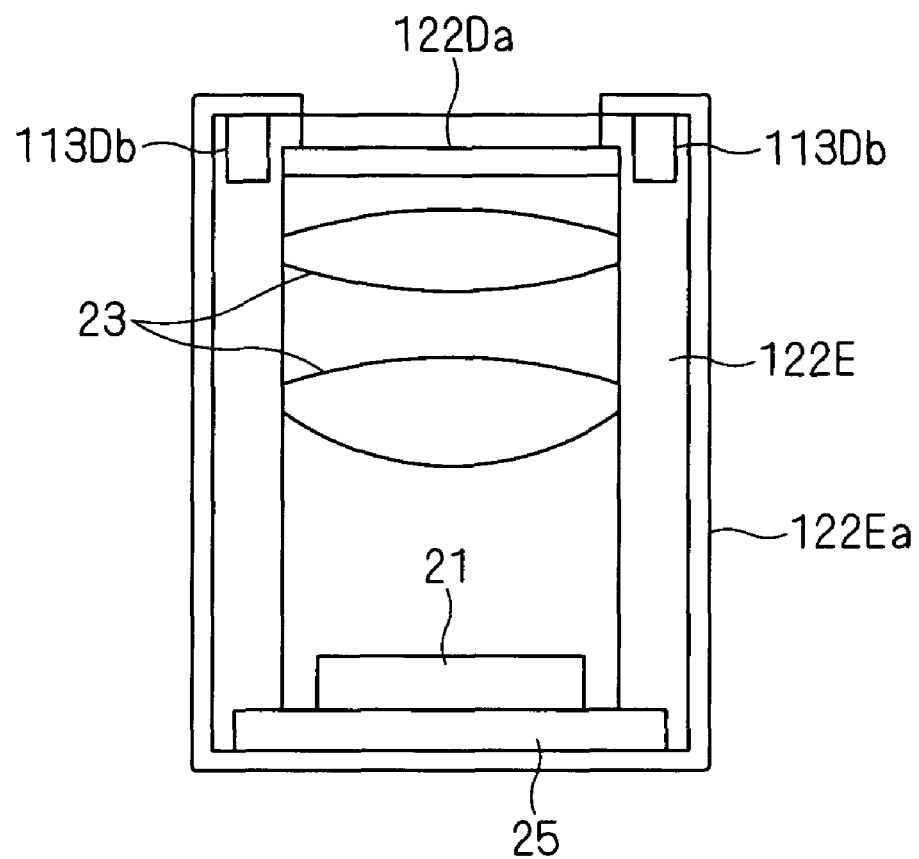

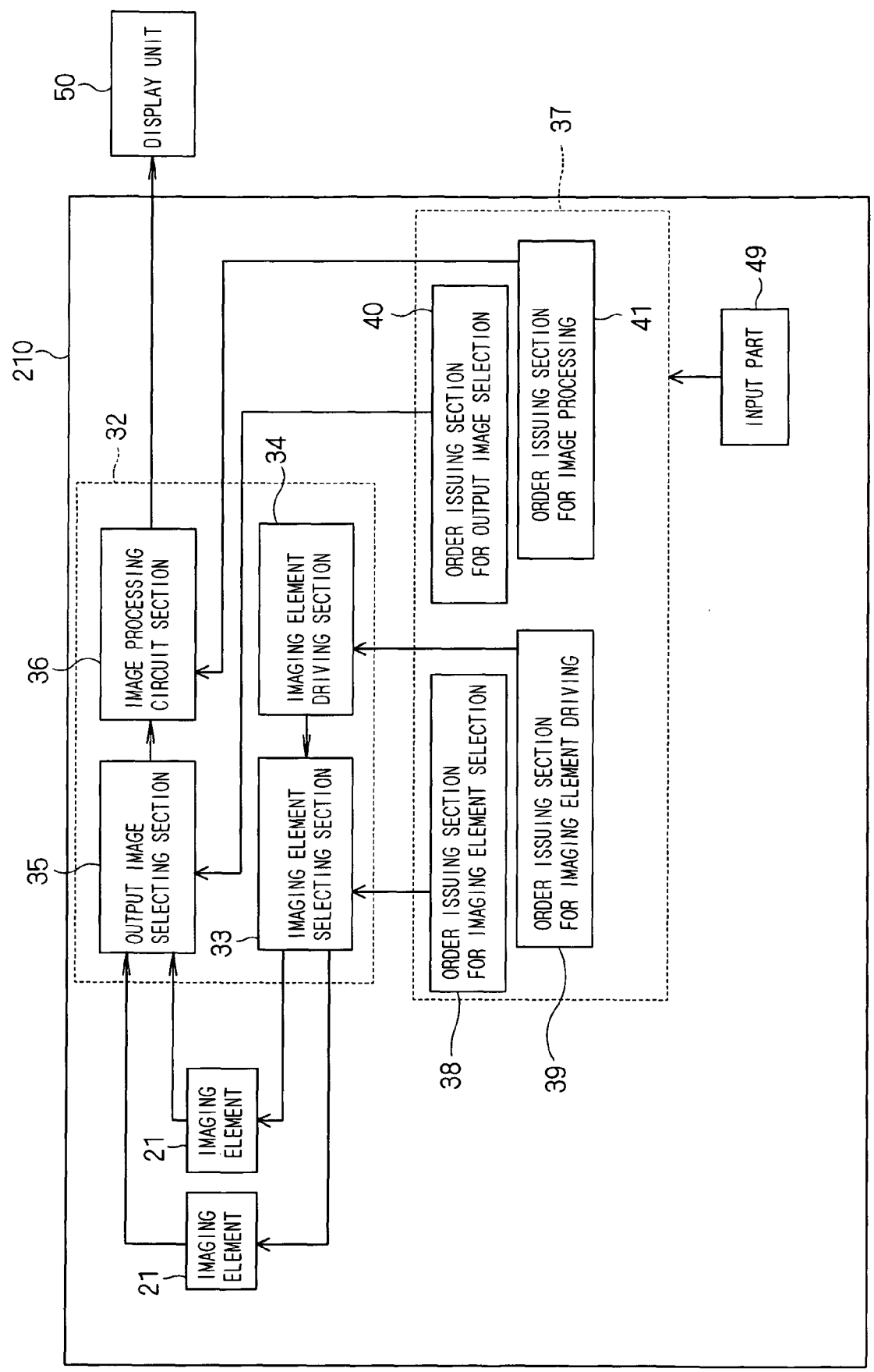

IMAGING DEVICE FOR DENTAL TREATMENT, AND INSTRUMENT UNIT FOR DENTAL TREATMENT WITH IMAGING DEVICE

TECHNICAL FIELD

The present invention relates to a technique of capturing an image of a site being treated during dental treatment thereof.

BACKGROUND ART

Japanese Patent Application Laid-Open No. 10-66677 discloses a conventional technique of incorporating an imaging device into an instrument for dental treatment.

In Japanese Patent Application Laid-Open No. 10-66677, an optical fiber imaging bundle and a CCD camera are incorporated into an instrument. One end of the optical fiber imaging bundle is provided with an objective lens system that is arranged near a treatment tool and a work area. Light emitted from a target site of imaging is guided through the objective lens and the optical fiber imaging bundle to the CCD camera, thereby capturing an image of the site.

Techniques similar to this are disclosed in Japanese Patent No. 3067854 and Japanese National Publication of Translation No. 4-503320.

Many sites cannot be viewed directly when they are treated within an oral cavity. Sites that are not directly visible include those that cannot morphologically be viewed due to the shape of a tooth or the shape inside the oral cavity, and those that cannot be viewed with the eyes of the operator of an operation (dentist). The operator should treat these invisible sites, or sites that are hard to be viewed.

The techniques disclosed in Japanese Patent Application Laid-Open No. 10-66677, Japanese Patent No. 3067854 and Japanese National Publication of Translation No. 4-503320 realize imaging of some of these invisible sites, or sites that are hard to be viewed.

However, in the techniques disclosed in Japanese Patent Application Laid-Open No. 10-66677, Japanese Patent No. 3067854 and Japanese National Publication of Translation No. 4-503320, imaging is conducted from a direction tilted from the axial direction of a cutting tool such as a dental drill. So, images of many sites cannot be captured by normal use thereof.

It is assumed for example that a hole is defined in a tooth, and then the deep part of the hole is treated, like as in the treatment of a pulp cavity in a tooth or in root canal treatment. In this case, the tooth itself, for example the outer edge of the crown of the tooth gets in the way, thereby making it difficult to illuminate the pulp cavity or the root canal and capture an image thereof. In order to capture an image of the pulp cavity or the root canal, light reflected from the pulp cavity or the root canal should be received. However, the reflected light is interrupted by the tooth itself, thereby making it impossible to receive light required for imaging. Or, the tooth itself may get in the way, so the emitted light cannot reach the pulp cavity or the root canal in the first place.

The structure according to the techniques disclosed in Japanese Patent Application Laid-Open No. 10-66677, Japanese Patent No. 3067854 and Japanese National. Publication of Translation No. 4-503320 contains an image guide such as an optical fiber for guiding light from a site being treated to an imaging element and the like. This means these techniques require a relatively expensive image guide, and the complicated structure of the instrument itself.

In view of the above, the present invention is intended to more reliably capture an image of a site being treated even during the treatment thereof, while realizing a simplified structure by eliminating an expensive image guide.

MEANS FOR SOLVING PROBLEMS

The present invention provides the following aspects in order to solve the aforementioned problems. A first aspect is an imaging device for dental treatment for use in an instrument for dental treatment with a head to which a rotary cutting tool can be attached. The imaging device for dental treatment comprises: an imaging module with at least an imaging element and an optical member; and a mounting section through which the imaging module is detachably attached to the instrument for dental treatment such that the imaging module is on the bottom side or on the lateral side of the head, and that the imaging module is in a posture that causes the imaging axis of the imaging module and the rotary axis of the rotary cutting tool to be substantially parallel. A lens or a diaphragm as the optical member may be provided in, or added to the imaging module.

According to a second aspect, the imaging device for dental treatment according to the first aspect further comprises one or multiple light-emitting parts for illumination purpose capable of being detachably attached to the bottom side or to the lateral side of the head. The light-emitting part for illumination purpose may be integrated with the imaging module, or may be provided independently of the imaging module.

According to a third aspect, in the imaging device for dental treatment according to the second aspect, especially the light-emitting part for illumination purpose is integrated with the imaging module. In this case, the light-emitting part for illumination purpose is provided in the imaging module. So, attachment and detachment of the imaging module necessarily results in simultaneous attachment and detachment of the light-emitting part for illumination purpose.

According to a fourth aspect, in the imaging device for dental treatment according to the second or third aspect, the light-emitting part for illumination purpose includes an illuminating part for normal imaging, and an excitation light illuminating part for use in a fluorescent image for extracting an abnormal site, and the illuminating part for normal imaging and the excitation light illuminating part for use in a fluorescent image can selectively emit light, or emit light at the same time.

According to a fifth aspect, in the imaging device for dental treatment according to any one of the first to fourth aspects, the mounting section has a fitting portion fixed to the imaging module, for allowing the imaging module to be fitted on the instrument for dental treatment.

According to a sixth aspect, in the imaging device for dental treatment according to the fifth aspect, the imaging module can be fitted on the bottom side or on the lateral side of the head through the fitting portion such that the imaging module is movable about the head by an operation with fingers.

According to a seventh aspect, in the imaging device for dental treatment according to any one of the first to sixth aspects, part of the imaging element or part of the imaging module is covered with a protective member made of heat-resistant resin.

According to an eighth aspect, in the imaging device for dental treatment according to any one of the first to seventh aspects, the imaging module includes multiple imaging modules.

In order to solve the aforementioned problems, in addition to the above-described aspects relating solely to the imaging device, the present invention provides aspects of an instrument unit to and from which an imaging device can be attached and detached. An instrument unit for dental treatment with an imaging device of a ninth aspect comprises: an instrument for dental treatment with a head to which a rotary cutting tool can be attached; and the imaging device for dental treatment according to any one of the first to eighth aspects that is detachably attached to the instrument for dental treatment.

According to a tenth aspect, in the instrument unit for dental treatment with an imaging device according to the ninth aspect, an interconnect line electrically connected to at least one of the imaging element and the light-emitting part for illumination purpose is buried in the instrument for dental treatment, or is detachably placed along the outer circumference of the instrument for dental treatment.

In order to solve the aforementioned problems, an instrument unit for dental treatment with an imaging device of an eleventh aspect comprises: an instrument for dental treatment with a head to which a rotary cutting tool can be attached; the imaging device for dental treatment according to the eighth aspect; and an image selection and output part for selectively outputting an image signal from the multiple imaging modules, the image selection and output part being provided in the instrument for dental treatment.

In order to solve the aforementioned problems, in addition to the above-described aspects of the instrument unit to and from which an imaging device can be attached and detached, the present invention provides aspects of an instrument unit to which an imaging device is integrally provided. An instrument unit for dental treatment with an imaging device of a twelfth aspect comprises: an instrument for dental treatment with a head to which a rotary cutting tool can be attached; and an imaging module with at least an imaging element and an optical member. The imaging module is integrally attached to the instrument for dental treatment such that the imaging module is on the bottom side or on the lateral side of the head, and that the imaging module is in a posture that causes the imaging axis of the imaging module and the rotary axis of the rotary cutting to be substantially parallel.

According to a thirteenth aspect, the instrument unit for dental treatment with an imaging device according to the twelfth aspect further comprises one or multiple light-emitting parts for illumination purpose integrally attached to the bottom side or to the lateral side of the head.

According to a fourteenth aspect, in the instrument unit for dental treatment with an imaging device according to the thirteenth aspect, the light-emitting part for illumination purpose is integrated with the imaging module.

According to a fifteenth aspect, in the instrument unit for dental treatment with an imaging device according to the thirteenth or fourteenth aspect, the light-emitting part for illumination purpose includes an illuminating part for normal imaging, and an excitation light illuminating part for use in a fluorescent image for extracting an abnormal site, and the illuminating part for normal imaging and the excitation light illuminating part for use in a fluorescent image can selectively emit light, or emit light at the same time.

According to a sixteenth aspect, in the instrument unit for dental treatment with an imaging device according to any one of the twelfth to fifteenth aspects, an interconnect line electrically connected to at least one of the imaging element and the light-emitting part for illumination purpose is buried in the instrument for dental treatment, or is placed along the outer circumference of the instrument for dental treatment.

According to a seventeenth aspect, in the instrument unit for dental treatment with an imaging device according to any one of the twelfth to sixteenth aspects, part of the imaging element or part of the imaging module is covered with a protective member made of heat-resistant resin.

According to an eighteenth aspect, in the instrument unit for dental treatment with an imaging device according to any one of the twelfth to seventeenth aspects, the imaging module includes multiple imaging modules.

According to a nineteenth aspect, the instrument unit for dental treatment with an imaging device according to the eighteenth aspect further comprises an image selection and output part for selectively outputting an image signal from the multiple imaging modules.

EFFECT OF THE INVENTION

The imaging device for dental treatment of the first aspect comprises the imaging module and the mounting section. When the imaging device for dental treatment is attached through the mounting section to the bottom side or to the lateral side of the head, the imaging axis of the imaging module and the rotary axis of the rotary cutting tool become substantially parallel. This allows simplification of a structure without using an expensive image guide that is hard to be placed on the instrument as it has low resistance to cracking, has large dimensions, and requires delicate positioning. The imaging module is arranged on the bottom side or on the lateral side of the head, and the imaging axis of the imaging module and the rotary axis of the rotary cutting tool are substantially parallel. Further, the range of imaging by the imaging module has a limited view angle even when the imaging axis and the rotary axis are substantially parallel. So, an image of the leading end of the rotary cutting tool can be captured by the imaging module. Further, a part existing around the rotary cutting tool is unlikely to interfere with imaging, so that an image of a site being treated can more reliably be captured even during the treatment with the rotary cutting tool. The treatment with the rotary cutting tool may be possible not only by its rotary motion about the rotary axis, but also by its vertical motion, or by its twist motion in which the rotary cutting tool repeatedly makes turns to the right and to the left that fall short of a 360-degree roll. The present invention is intended mainly to make the rotary axis of the rotary cutting tool and the imaging axis to be substantially parallel, and places no importance on the motion of the rotary cutting tool in order to give treatment. That is, as long as the rotary axis and the imaging axis are substantially parallel, the present invention is carried out regardless of the motion of the cutting tool with the rotary axis.

The part existing around the rotary cutting tool mentioned above is for example a crown when the interior of a root canal is a target site of treatment. In Japanese Patent Application Laid-Open No. 10-66677 and the like, this part is likely to interfere with imaging. The head, especially the lateral side of the head has a subtle curve in many cases, so the imaging axis of the imaging module may not be parallel in a strict sense to the rotary axis of the cutting tool. Even in this case, the imaging module is attached such that the part existing around the cutting tool does not interfere with imaging, and an image of a site being treated is more reliably captured, thereby achieving an object of the present invention. The relationship between the imaging axis and the rotary axis in this case is called "substantially parallel relationship" in the present description.

In the imaging device for dental treatment of the second aspect, a site being treated is illuminated by one or multiple light-emitting parts for illumination purpose. So, light required for imaging can be applied directly to a site targeted for imaging from the bottom side or the lateral side of the head of the instrument for dental treatment. This allows the optical axis of emitted light as well as the imaging axis to be substantially parallel to the rotary axis of the cutting tool. Thus, the part existing around the rotary cutting tool is unlikely to interfere with illumination and imaging. Further, when multiple light-emitting parts for illumination purpose are provided, light required for imaging can be supplied from several directions. This prevents interference of an obstacle to thereby realize effective illumination.

According to the third aspect, the light-emitting part for illumination purpose is integrated with the imaging module. This allows the imaging module together with the light-emitting part for illumination purpose as one unit to be attached easily to the instrument for dental treatment. This also makes control of the positions and angles of the imaging element and the light-emitting part for illumination purpose relative to each other easy that is required for control of a range of imaging and a range of illumination. Also, attachment and detachment of the imaging module necessarily results in attachment and detachment of the light-emitting part for illumination purpose.

According to the fourth aspect, the illuminating part for normal imaging and the excitation light illuminating part for use in a fluorescent image can selectively emit light, or emit light at the same time. This allows emission of light that is responsive to the needs of imaging. As an example; when illumination light is turned off and only excitation light is applied, a diseased site targeted for treatment and a sound site that is not targeted for treatment are distinguished from each other according to the degree of emission of fluorescent light. So, the targeted site can be treated while it is clearly recognized visually. An optical filter for cutting out excitation light may be provided to the imaging module in order to obtain a favorable fluorescent image.

In the imaging device for dental treatment of the fifth aspect, the imaging module can easily be attached detachably to the instrument for dental treatment.

According to the sixth aspect, the imaging module is allowed to move about the head by an operation with fingers. This enhances convenience as it allows change of an imaging direction.

According to the seventh aspect, part of the imaging element or part of the imaging module is covered with a protective member made of heat-resistant resin. So, resistance to water and resistance to autoclaving are enhanced.

According to the eighth aspect, an image of a site being treated is captured from each of the multiple imaging modules. So, ranges of imaging by imaging elements complement each other. More specifically, when an obstacle to imaging is present in the range of imaging by one imaging element, this obstacle does not fall within the range of imaging by a different imaging element. So, an image of a site being treated can be captured appropriately, thereby lowering the probability of occurrence of a situation where an image of a site being treated cannot be captured.

The instrument unit for dental treatment with an imaging device of the ninth aspect comprises the instrument for dental treatment, and the imaging device for dental treatment that is detachably attached to the instrument. So, an image of a site being treated is captured during treatment with the instrument while simplification of a structure is realized without using an expensive image guide. Further, the imaging module is arranged on the bottom side or on the lateral side of the head, and the imaging axis of the imaging module and the rotary axis of the rotary cutting tool are substantially parallel. Thus a part existing around the rotary cutting tool is unlikely to interfere with imaging, so that an image of a site being treated can more reliably be captured even during the treatment with the rotary cutting tool.

According to the tenth aspect, at least one of the imaging element and the light-emitting part for illumination purpose is electrically connected to a different device through the buried interconnect line, or through the interconnect line detachably placed along the outer circumference.

According to the eleventh aspect, an image signal is selectively output from the multiple imaging modules. This allows output of a desirable image as one of images the multiple imaging elements can capture.

The imaging device for dental treatment with an imaging device of the twelfth aspect comprises the instrument for dental treatment and the imaging element. The imaging element is integrally attached to the instrument for dental treatment such that the imaging element is on the bottom side or on the lateral side of the head, and that the imaging module is in a posture that allows the imaging axis of the imaging module and the rotary axis of the rotary cutting tool to be substantially parallel. This allows simplification of a structure without using an expensive image guide that is hard to be placed on the instrument. Further, the imaging module is arranged on the bottom side or on the lateral side of the head, and the imaging axis of the imaging module and the rotary axis of the rotary cutting tool are substantially parallel. Thus, a part existing around the rotary cutting tool is unlikely to interfere with imaging, so that an image of a site being treated can more reliably be captured even during the treatment with the rotary cutting tool.

In the imaging device for dental treatment with an imaging device of the thirteenth aspect, a site being treated is illuminated by one or multiple light-emitting parts for illumination purpose. So, light required for imaging can be applied directly to a site targeted for imaging from the bottom side or the lateral side of the head of the instrument for dental treatment. This allows the optical axis of emitted light as well as the imaging axis to be substantially parallel to the rotary axis of the cutting tool. Thus, the part existing around the rotary cutting tool is unlikely to interfere with illumination and imaging. Further, when multiple light-emitting parts for illumination purpose are provided, light required for imaging can be supplied from several directions. This prevents interference of an obstacle to thereby realize effective illumination.

According to the fourteenth aspect, the light-emitting part for illumination purpose is integrated with the imaging module. This makes control of the positions and angles of the imaging element and the light-emitting part for illumination purpose relative to each other easy.

According to the fifteenth aspect, the illuminating part for normal imaging and the excitation light illuminating part for use in a fluorescent image can selectively emit light, or emit light at the same time. This allows emission of light that is responsive to the needs of imaging. As an example, when illumination light is turned off and only excitation light is applied, a diseased site targeted for treatment and a sound site that is not targeted for treatment are distinguished from each other according to the degree of emission of fluorescent light. So, the targeted site can be treated while it is clearly recognized visually. An optical filter for cutting out excitation light may be provided to the imaging module in order to obtain a favorable fluorescent image.

According to the sixteenth aspect, at least one of the imaging element and the light-emitting part for illumination purpose is electrically connected to a different device through the buried interconnect line, or through the interconnect line detachably placed along an outer circumference. This realizes a way of use in which the imaging element and the light-emitting part for illumination purpose are connected to power sources from which they are given power, or in which an image signal output from the imaging element is connected to an external display.

According to the seventeenth aspect, part of the imaging element or part of the imaging module is covered with a protective member made of heat-resistant resin. So, resistance to water and resistance to autoclaving are enhanced.

According to the eighteenth aspect, an image of a site being treated is captured from each of the multiple imaging modules, and a desirable image is obtained from the captured images.

According to the nineteenth aspect, an image signal is selectively output from the multiple imaging modules. This allows output of a desirable image as one of images the multiple imaging elements can capture.

BRIEF DESCRIPTION OF DRAWINGS

FIG. 3 is an explanatory view showing an imaging and treatment system in its entirety according to the present invention;

FIG. 32 is a sectional view of another modification of an imaging module;

FIG. 55 is a front view showing a block diagram according to a modification.

MODE(S) FOR CARRYING OUT THE INVENTION

{Description of Tooth as Exemplary Target of Application and Description of Premise}

Figure 1:
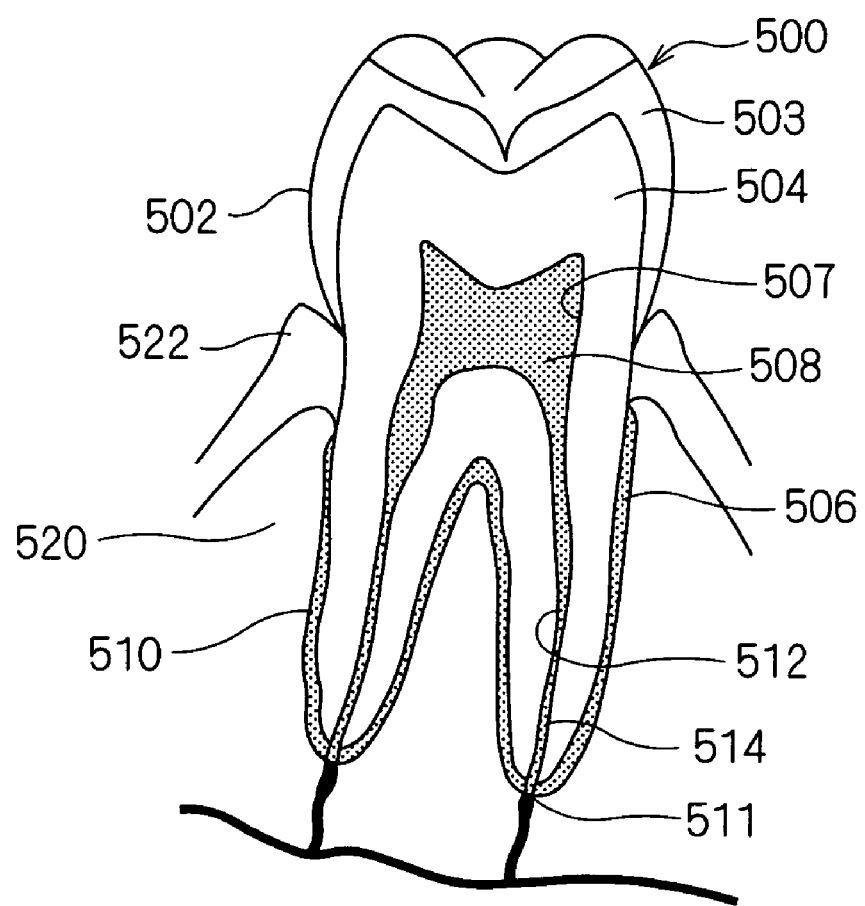
FIG. 1 is a sectional view of the structure of a human tooth.

Prior to description of embodiments, the structure of a tooth as an exemplary target of application is described first. FIG. 1 is a sectional view of the structure of a human tooth. A human tooth 500 includes a crown 502 exposed in an oral cavity, and a root 510 extending from the crown 502. The surface of the root 510 is covered with a periodontal membrane not shown. The crown 502 is constructed of enamel 503, dentin 504, and others. A pulp chamber 507 is formed inside the crown 502. The root 510 is constructed of the dentin 504, cementum 506, and others, and is supported by alveolar bone 520 and gum 522. A root canal 512 is formed inside the root 510 such that it extends in a direction in which the root 510 extends. Pulps 508 and 514 inside the crown 502 and the root 510 are connected to blood vessels and nerves under the alveolar bone 520. The extreme tip of the root 510 facing the alveolar bone 520 is called an apex 511 (APEX), and an opening of the apex 511 facing the alveolar bone 520 is called an apical foramen.

The treatment of the tooth 500 involves various processes such as root canal enlargement, for example. The condition of the tooth 500 to be examined, and interrelationship between the tooth 500 and a treatment tool are observed during these processes. During the treatment, some sites are hard to be viewed directly by an operator who is responsible for the treatment. The sites that are not directly visible are generated by the shape of the tooth 500 itself, relationship among relative positions of the tooth 500, the treatment tool and the eyes of the operator, and the like. The operator is required to care even these sites that are not directly visible. With reference especially to root canal treatment, as is also called endodontic therapy, it is the treatment of the pulp chamber 507 and the root canal 512 inside the tooth 500. So, these sites are seriously hard to be viewed directly.

Figure 2:
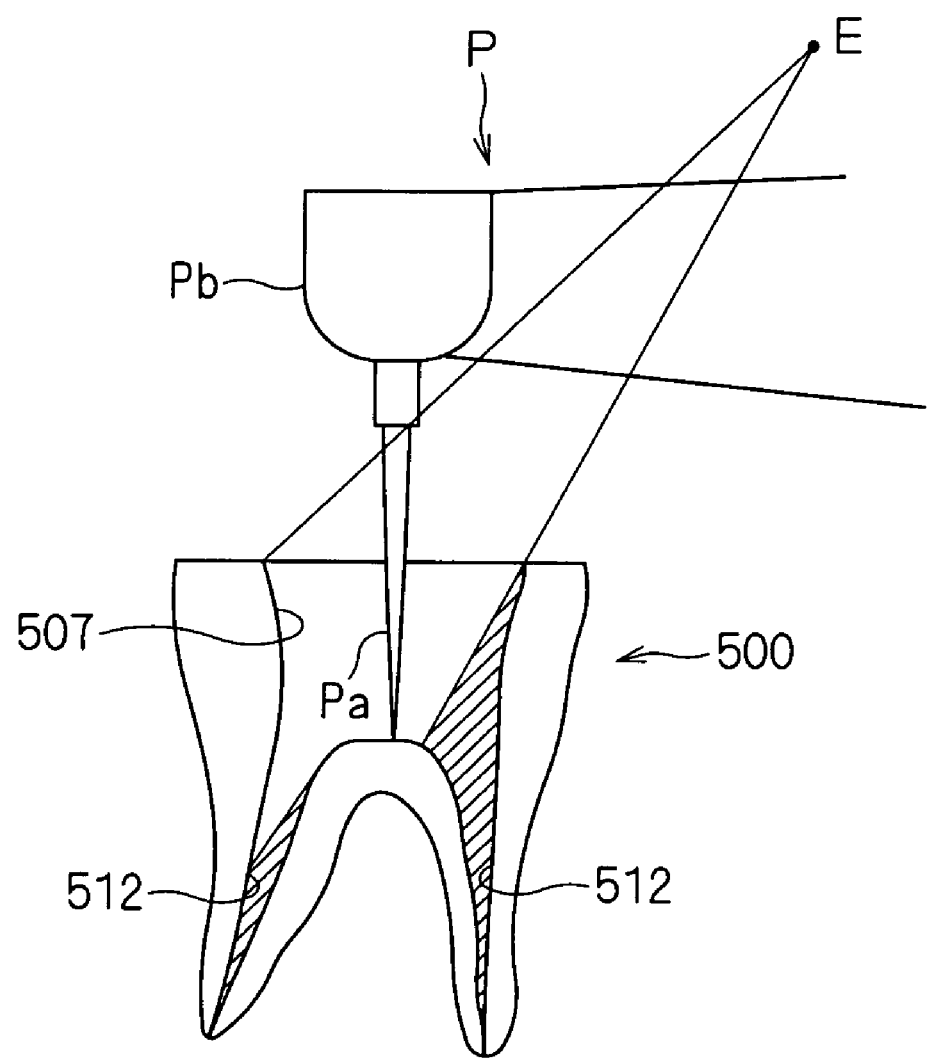
FIG. 2 is an explanatory view of a range that is hard to be viewed directly inside a tooth.

FIG. 2 is an explanatory view showing a directly visible range inside the tooth 500. As seen from FIG. 2, looking down from a position (see point E) obliquely above a hole defined in the crown 502 is necessary in order to observe the interior of the tooth 500. At this time, the pulp chamber 507, and especially the root canal 512 inside the tooth 500 are likely to be in a blind spot (see diagonally shaded area), so are seriously hard to be observed directly. Further, in the first place, light that is absolutely necessary for viewing the chamber 507 or the root canal 512 directly may not reach the chamber 507 or the root canal 512. In addition, presence of a substance inside the tooth 500 such as a cutting tool Pa of a root canal treatment appliance P, and presence of a head Pb of the root canal treatment appliance P above the tooth 500 during the root canal treatment also become obstacles that make it more difficult to observe the interior of the tooth 500.

In each of embodiments, it is described how an image of a site being treated is more reliably captured even during the aforementioned treatment.

First Embodiment

In the below, an instrument unit for dental treatment with an imaging device of a first embodiment is described.

The overall structure of an imaging and treatment system including the instrument unit for dental treatment with an imaging device is described first. FIG. 3 is an explanatory view of the imaging and treatment system in its entirety.

This system includes an instrument 11 for dental treatment, an imaging control unit 30, a display unit 50, and an instrument control unit 60. An imaging device for dental treatment including imaging modules 20 (see FIG. 7) each with an imaging element 21 and a lens (optical member) 23, and a mounting section 26 (see FIG. 4) is incorporated into the instrument 11 for dental treatment, thereby forming an instrument unit 10 for dental treatment with an imaging device. The imaging element 21, the lens 23, the mounting section 26 and others are described later with reference to FIG. 4. While a lens is cited as an example of the optical member, it may be replaced by another optical member such as a mirror or a diaphragm, or a mirror or a diaphragm may be added, which are also applicable to the following description.

A rotary cutting tool 18 attached to the instrument 11 for dental treatment is a treatment tool used for tooth treatment. Here, the description is given based on the assumption that the instrument 11 for dental treatment is a root canal treatment appliance that is mainly intended for root canal enlargement.

The instrument control unit 60 includes a microcomputer with a CPU, a ROM, a RAM and others, and performs a predetermined process based on a software program stored in advance therein. Here, the instrument control unit 60 is connected through a cable 62 with a drive line for the instrument 11 for dental treatment to the instrument 11 for dental treatment. The instrument control unit 60 is responsible for drive control of the instrument 11 for dental treatment such as on/off control of rotation and speed of rotation of a file 18 as a root canal enlargement tool, for example. The instrument control unit 60 may also function to measure a root canal length by using a file and the like as a measuring electrode. All of or part of the function of the instrument control unit 60 may be incorporated into the instrument 11 for dental treatment. As a matter of course, the instrument control unit 60 and the imaging control unit 30 may be formed as one unit.

The imaging control unit 30 is connected through a cable 64 with drive lines and image signal output lines for the imaging elements 21 to the instrument control unit 60. The imaging control unit 30 is also connected through a cable 66 with an image signal output line to the display unit 50. The imaging control unit 30 controls driving of the imaging elements 21 of the imaging modules 20 (see FIG. 4) attached to the instrument 11 for dental treatment. The imaging control unit 30 also performs a predetermined image processing on image signals received from the imaging elements 21, and outputs the resultant image signals to the display unit 50. All of or part of the function of the imaging control unit 30 may also be incorporated into the instrument 11 for dental treatment.

The display unit 50 is constructed of a liquid crystal display, an organic EL display, a personal computer, and the like. An image is displayed on the display unit 50 based on an image signal output from the imaging control unit 30.

A head-mounted display unit 50B may be employed as a display unit. The head-mounted display unit 50B may take the place of the display unit 50, or may be provided separately from the display unit 50.

A signal may be transmitted without wires but by using Bluetooth and the like between the instrument unit 10 for dental treatment with an imaging device, the imaging control unit 30, the display unit 50, and the instrument control unit 60. In this case, a radio frequency is preferably changed where appropriate. Wireless transmission of an image signal especially between the imaging control unit 30 and the head-mounted display unit 50B lightens restrictions on the action of an operator wearing the head-mounted display unit 50B, by which excellent convenience of handling by the operator is achieved. The handling by the operator is made easier by transmitting an image signal without wires between the imaging control unit 30 and the head-mounted display unit 50B after the functions of both the instrument control unit 60 and the imaging control unit 30 are incorporated into the instrument unit 10 for dental treatment with an imaging device.

Figure 4:
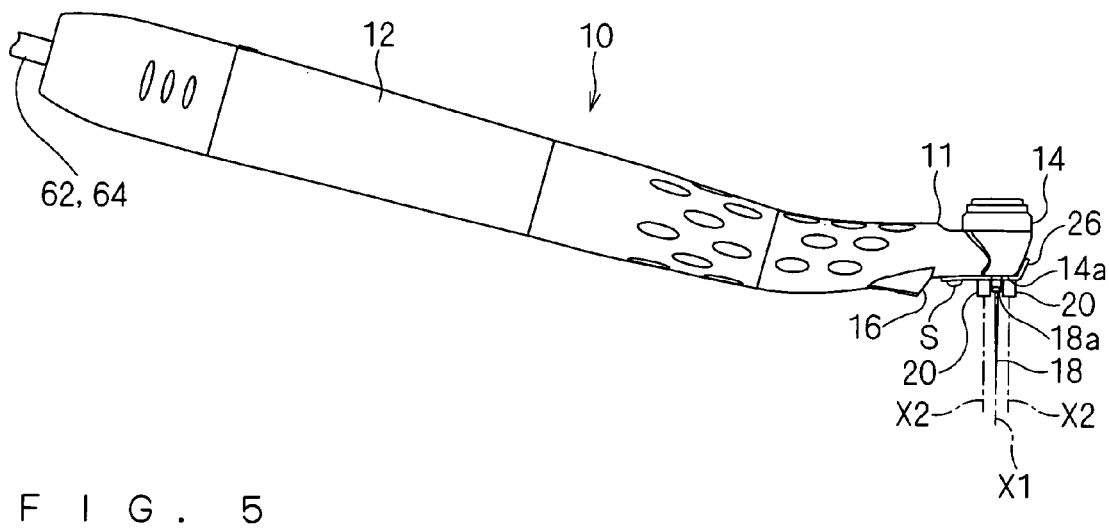
FIG. 4 is a side view of an instrument unit for dental treatment with an imaging device according to a first embodiment of the present invention.
Figure 5:
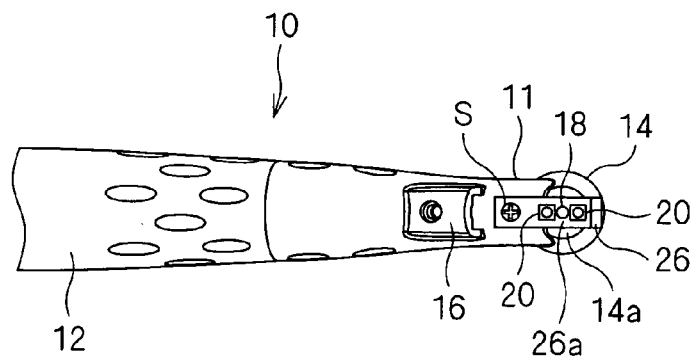
FIG. 5 is a bottom plan view of this instrument unit for dental treatment with an imaging device.
Figure 6:
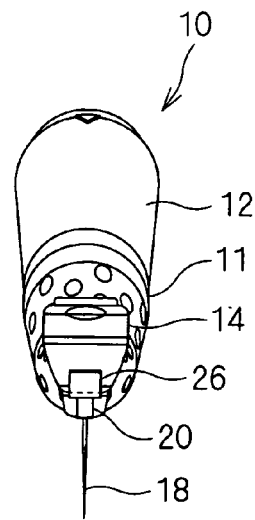
FIG. 6 is a front view of this instrument unit for dental treatment with an imaging device.

FIGS. 4 to 6 are a side view, a bottom plan view, and a front view of the instrument unit 10 for dental treatment with an imaging device.

The instrument unit 10 for dental treatment with an imaging device is formed by incorporating the imaging device for dental treatment with the imaging elements 21 and the mounting section 27 into the instrument 11 for dental treatment.

The instrument 11 for dental treatment includes an instrument body 12 and a head 14.

The instrument body 12 is formed into a member with a continuous length that an operator can grip by hand. The instrument body 12 has one end portion provided with the head 14, and an opposite end portion from which the cables 62 and 64 extend. An illuminating part 16 that can illuminate the front end portion of the rotary cutting tool 18 described later is attached to a position near the one end portion of the instrument body 12. A light-emitting diode, a light bulb, or the light-exiting end of a light guide for guiding light from a light emitter provided in the instrument body 12, may be used as the illuminating part 16. The illuminating part 16 is a part the instrument 11 for dental treatment is normally equipped with regardless of whether or not an imaging module is attached thereto. The illuminating part 16 illuminates space inside an oral cavity during treatment, and emits light regardless of whether or not an imaging operation is being performed by the imaging elements 21.

The structure of the head 14 is such that the rotary cutting tool 18 such as a reamer or a file can be attached thereto. The rotary cutting tool 18 includes various types of tools for cutting a tooth by their rotary motions. Treatment with the rotary cutting tool 18 may be possible not only by its rotary motion, but also by its vertical motion, or by its twist motion in which the rotary cutting tool 18 repeatedly makes turns to the right and to the left that fall short of a 360-degree roll. In the below, a side of the head 14 to which the rotary cutting tool 18 is provided to extend along its rotary axis X1 is called the lower end or bottom side of the head, and a side opposite thereto is called the upper end of the head.

More specifically, the shape of the head 14 is such that it is gradually reduced in diameter in a direction toward its one end (lower end), that it has a substantially circular plane surface 14a at this end, and that it is integrally coupled at its lateral side to the instrument body 12. A rotary driving mechanism such as a micro-motor or a turbine is provided inside the instrument body 12 or the head 14. The rotary motion of the rotary driving mechanism is transmitted through a gear and the like to the rotary cutting tool 18. The rotary cutting tool 18 such as a reamer or a file is detachably attached, in a posture in which the lower end thereof extends outward, through a shank 18a at its base end to a portion that is nearly the center of the substantially circular plane surface 14a of the head 14 defined at its lower end. The rotary driving force of the aforementioned rotary driving mechanism is transmitted through the shank 18a to the rotary cutting tool 18, thereby causing the rotary cutting tool 18 to rotate. This allows treatment of a tooth such as cutting by using the rotary cutting tool.

The rotary axis X1 of the rotary cutting tool 18 is an axis with respect to which the rotary cutting tool 18 is caused to rotate as the above-described rotary driving mechanism is driven.

The imaging modules 20 are detachably attached through the mounting section 26 to the head 14 of the instrument 11 for dental treatment.

Figure 7:
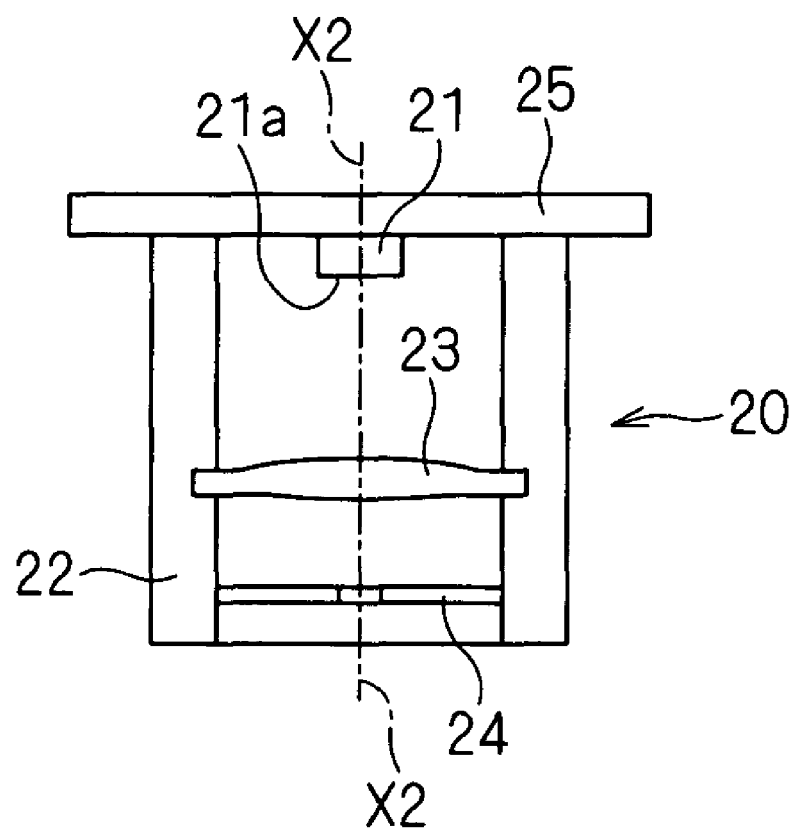
FIG. 7 is a sectional view of an imaging module.

FIG. 7 is a sectional view of the imaging module 20. The imaging module 20 includes the imaging element 21 such as a CCD and the like. As is described later, the imaging module 20 is sufficiently reduced in size to an extent that it does not interfere with treatment with the rotary cutting tool 18 even when the imaging module 20 is attached to the lower end portion or the lateral side of the head 14.

More specifically, the imaging module 20 includes a substantially cylindrical (here, substantially rectangular cylindrical) lens barrel 22, the lens 23 and a diaphragm 24 arranged in the lens barrel 22, a board 25 and the imaging element 21. As a matter of course, the structure and the material of the imaging module are not limited to those shown in FIG. 7. As an example, the diaphragm 24 may be unnecessary in some cases.

The lens barrel 22 is made of heat-resistant resin, and is formed into a substantially cylindrical shape with openings at opposite ends. The lens barrel 22 may alternatively be made of metal. The lens barrel 22 is preferably made of a material with high steam resistance in order to withstand an autoclave sterilization process.

The diaphragm 24 is placed in one end portion of the lens barrel 22. The lens 23 is placed between the diaphragm 24 and the imaging element 21 in the lens barrel 22. An image is formed by the lens 23 on an imaging surface 21a of the imaging element 21 while external light is regulated by the diaphragm 24. The lens 23 may be constructed of multiple lenses. The positions of the lens 23 and the diaphragm 24 may appropriately be changed according to their optical characteristics. Or, positional relationship between the diaphragm 24 and the lens 23 may be reversed. Further, when an excitation light illuminating part described later is used, an optical filter may be provided that cuts out excitation light reflected by a subject of imaging, extracts fluorescent light, and captures an image thereof.

The imaging element 21 is constructed of a CCD, a CMOS and the like, and has an integrated structure of an image sensor with the imaging surface 21a, a driving circuit for the sensor, and others. This integrated structure is preferably sealed with resin, for example. The imaging element 21 is fixedly mounted to one main surface of the board 25, in a posture in which the imaging surface 21a of the imaging element 21 is placed to face toward the direction in which this main surface faces. With the imaging surface 21a facing toward the opening at one end portion of the lens barrel 22, the board 25 is attached at the opening at the other end portion of the lens barrel 22 such that the imaging element 21 is placed at the opening at the other end portion of the lens barrel 22.

The form of the imaging module 20 is such that the imaging element 21, especially part of the imaging element 21 including the imaging surface 21a is covered with the lens barrel 22 as a protective member made of heat-resistant resin.

The imaging module 20 has a central axis of an imaging area that is defined as an imaging axis X2. Here, an axis passing through a point that is nearly the center of the imaging surface 21a of the imaging element 21 contained in the imaging module 20, while extending in a direction substantially vertical to the imaging surface 21a, is the imaging axis X2 of the imaging module 20 (imaging element 21). While two imaging modules 20 are provided in this example, the number of imaging modules 20 may be one, or three or higher.

Referring back to FIGS. 4 to 6, the structure of the mounting section 26 is such that it causes the imaging modules 20 to be detachably attached to the instrument 11 for dental treatment, in such a way that the imaging modules 20 are placed on the bottom side of the head 14, and that the imaging axes X2 of the imaging modules 20 and the rotary axis X1 of the rotary cutting tool 18 are substantially parallel. The rotary axis X1 and the imaging axes X2 are preferably as close as possible.

Here, the structure of the mounting section 26 is such that it is detachably attached with a screw S to the instrument 11 for dental treatment.

More specifically, the mounting section 26 is made of resin and the like, and is formed into a substantially elongated plate that bends in such a way that the mounting section 26 can extend from the one end portion of the instrument body 12, passing through the portion that is nearly the center of the substantially circular plane surface 14a of the head 14, to the lateral side of the head 14 opposite to the instrument body 12. As a matter of course, the mounting section 26 may be formed in its entirety from an electrical board. A hole 26a through which the shank 18a can be loosely fitted is defined in a position that is nearly the center of the longitudinal direction of the mounting section 26. Further, the two imaging modules 20 are provided as one unit to the mounting section 26 in such a way that the hole 26a is held between the two imaging modules 20.

A screw clearance hole is defined in one end portion of the mounting section 26 on the side with respect to the instrument body 12. Further, a screw fixing hole corresponding to the screw clearance hole is defined in the instrument body 12.

With the mounting section 26 placed to surround the head 14 of the instrument 11 for dental treatment so that the two imaging modules 20 will be arranged around the shank 18a, the screw S is driven through the screw clearance hole into the screw fixing hole. As a result, the imaging modules 20 are attached through the mounting section 26 to the instrument 11 for dental treatment. When the screw S in this state is loosened and then removed, the imaging modules 20 are detached from the instrument 11 for dental treatment.

The imaging modules 20 may also be arranged on the lateral side of the head 14, as long as the imaging axes X2 and the rotary axis X1 are substantially parallel, and the imaging modules 20 can perform imaging in a direction of the leading end of the rotary cutting tool 18. As already described, the head 14 is gradually reduced in diameter in a direction toward its one end (lower end), while having a subtle curve in some cases. So, when the imaging modules 20 are on the lateral side of the head 14, the imaging axes X2 and the rotary axis X1 may not be parallel in a strict sense. In this case, however, the imaging axes X2 and the rotary axis X1 are still substantially parallel. So, the imaging modules 20 can perform imaging in a direction of the leading end of the rotary cutting tool 18.

As long as the imaging modules 20 are arranged on the bottom side or the lateral side of the head 14, the mounting section 26 itself may be arranged on a different part of the head 14, or may be attached for example to the instrument body 12 and the like.

The reason for the substantially parallel positional relationship between the imaging axes X2 and the rotary axis X1 is that, an image of the leading end and its vicinity of the rotary cutting tool 18 can be captured generally by the imaging in the axial direction of the rotary cutting tool 18, without interference of an obstacle such as other part of a tooth. In this case, what is called a root canal orifice can be observed in such a way that it is looked down in a direction of the longer axis of a root. So, the substantially parallel positional relationship between the imaging axes X2 and the rotary axis X1 is not necessarily limited to exactly parallel positional relationship therebetween. Given that the aforementioned normal endodontic therapy is to be performed, this relationship also includes the case where the imaging axes X2 and the rotary axis X1 are substantially parallel to an extent that allows image capture of the leading end of the rotary cutting tool 18 without interference of an obstacle such as other part of a tooth.

Figure 8:
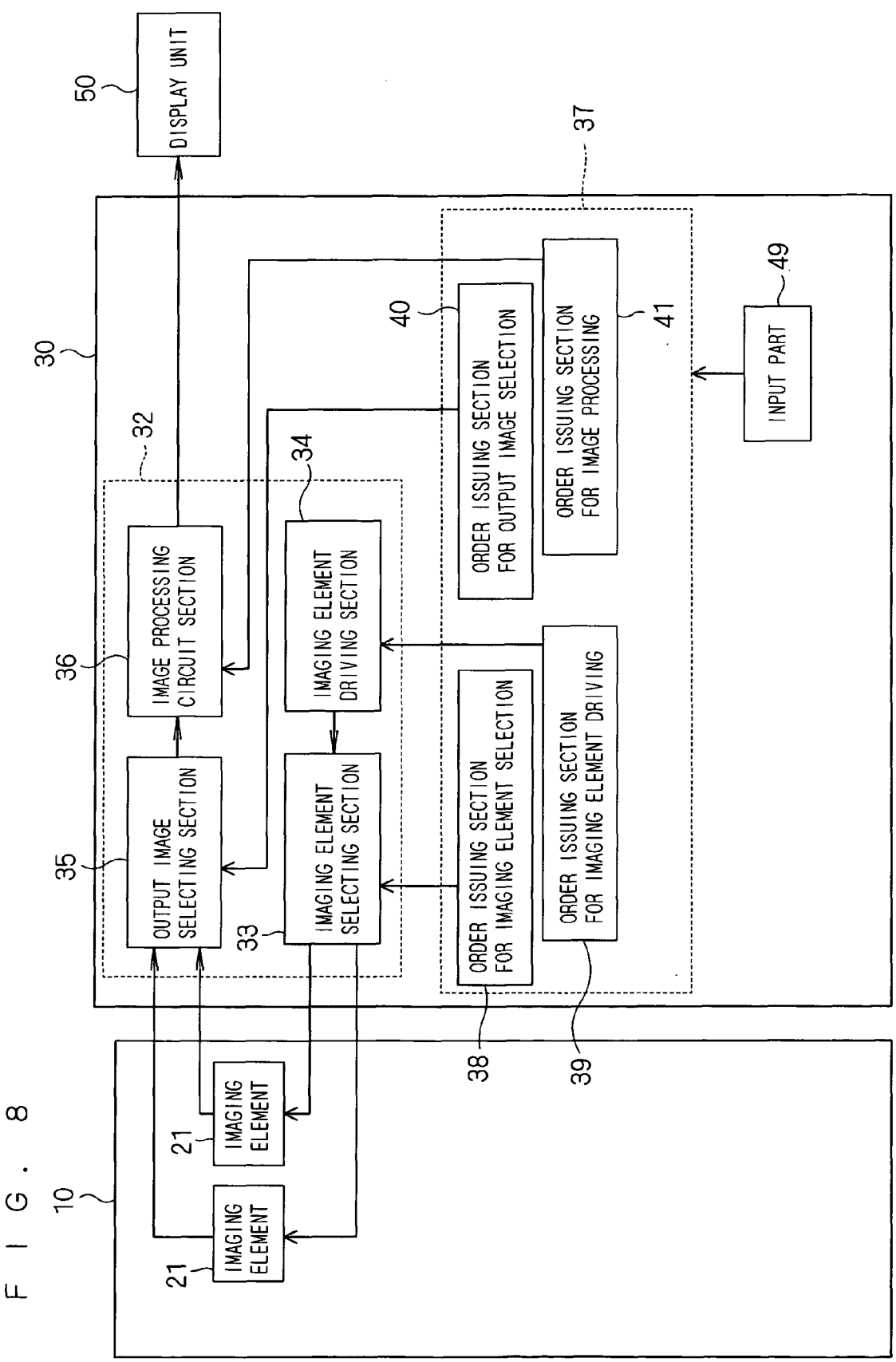
FIG. 8 is a block diagram including the instrument unit for dental treatment with an imaging device, an imaging control unit, and a display unit.

FIG. 8 is a block diagram including the instrument unit 10 for dental treatment with an imaging device, the imaging control unit 30 and the display unit 50 that constitute the imaging and treatment system. General-purpose functions such as a power source are not shown in FIG. 8.

As shown in this figure, the instrument unit 10 for dental treatment with an imaging device includes multiple (here, two) imaging elements 21 contained in the imaging modules 20.

The imaging control unit 30 includes an image control part 32, a control order issuing part 37, and an input part 49. The imaging control unit 30 includes a power source and a power switch not shown, and is put into operation upon receipt of electric power from the power source in response to on/off control of the power switch.

The input part 49 is capable of receiving instructions from an operator and the like. Here, the input part 49 is capable of receiving instructions to select at least one from the multiple imaging elements 21. A mechanical switch, and those structures capable of receiving instructions from the operator and the like including that for receiving instructions through a predetermined entry screen, are all applicable as the input part 49. A signal responsive to instructions received by the input part 49 is given to the control order issuing part 37.

The control order issuing part 37 is constructed of a microcomputer with a CPU, a ROM, a RAM and others, and controls the image control part 32 in response to a signal given from the input part 49. Here, the control order issuing part 37 has functions of an order issuing section 38 for imaging element selection, an order issuing section 39 for imaging element driving, an order issuing section 40 for output image selection, and an order issuing section 41 for image processing. When instructions to select one from the multiple imaging elements 21 are given through the input part 49, the control order issuing part 37 causes the order issuing section 38 for imaging element selection to specify the selected imaging element 21, and to issue an order for selection to an imaging element selecting section 33 in response to the instructions. The control order issuing part 37 also causes the order issuing section 39 for imaging element driving to issue an order for driving to an imaging element driving section 34. The control order issuing part 37 also causes the order issuing section 40 for output image selection to specify the selected imaging element 21, and to issue an order for selection to an output image selecting section 35. Further, the control order issuing part 37 causes the order issuing section 41 for imaging processing to issue an order for image processing to an image processing circuit section 36.

The image control part 32 includes the imaging element selecting section 33, the imaging element driving section 34, the output image selecting section 35, and the image processing circuit section 36.

The imaging element driving section 34 is constructed of a driving circuit and the like for on-off control of driving of the imaging elements 21. The imaging element driving section 34 outputs a driving signal in response to an order for driving issued by the order issuing section 39 for imaging element driving. The imaging element selecting section 33 is constructed of a selector circuit and the like with one input and multiple (here, two) outputs. The imaging element selection section 33 selects one imaging element 21 in response to an order for selection issued by the imaging element selecting section 33, and outputs a driving signal given from the imaging element driving section 34 to the selected imaging element 21.

The image processing circuit section 36 is constructed of an integrated circuit and the like responsible for image processing. In response to an order for image processing issued by the order issuing section 41 for image processing, the image processing circuit section 36 performs processing such as A/D conversion or image correction on an image signal received from the imaging element 21, and outputs the same as an image signal capable of being displayed on the display unit 50.

The output image selecting section 35 is constructed of a selector circuit and the like with multiple (here, two) inputs and one output. The output image selecting section 35 selects one imaging element 21 in response to an order for selection issued by the order issuing section 40 for output image selection, identifies an input signal received from the selected imaging element 21, and applies the selected image signal to the image processing circuit section 36. The output image selecting section 35 and the image processing circuit section 36 constitute an image selection and output part for selectively outputting an image signal from the multiple imaging elements 21.

The image processing circuit section 36 may be provided for each of the multiple imaging elements 21, and images captured by the multiple imaging elements 21 may be displayed at the same time. Or, these images may be coupled, and then displayed as one image. In these cases, an operator enters instructions through the input part 49 to use all of the multiple imaging elements 21. The control by the control order issuing part 37 responsive to these instructions is such that all of the multiple imaging elements 21 are driven. Then, image signals obtained from the multiple imaging elements 21 are transmitted to the multiple image processing circuit sections 36, or are transmitted for storage to a memory not shown. The structure described so far allows multiple images obtained respectively from the multiple imaging elements to be displayed at the same time or selectively on the display unit 50, or to be coupled and then displayed as one image on the display unit 50. In order to display multiple images at the same time, the display unit 50 may be divided and each image may be displayed in one section. Or, images may be displayed independently in the right and left display sections of the head-mounted display 50B.

Part of or all of the function of the imaging control unit 30 may be incorporated into either the instrument unit 10 for dental treatment with an imaging device or the instrument control unit 60, or both of them.

In the imaging and treatment system including the instrument unit 10 for dental treatment with an imaging device, when an order to start imaging is given after one imaging element 21 is specified through the input part 49, a driving signal is given from the imaging element driving section 34 through the imaging element selecting section 33 to the specified imaging element 21. Then, the specified imaging element 21 captures an image. An image signal from the specified imaging element 21 is thereafter given through the output image selecting section 35 to the image processing circuit section 36, is subjected to predetermined image processing in the image processing circuit section 36, and is then output to the display unit 50. As a result, the image captured by the specified imaging element 21 is displayed on the display unit 50. Each of the number of imaging elements 21 to be specified at a time, and the number of images to be captured by the specified imaging element 21 and to be displayed on the display unit 50 at a time, is not always limited to one.

Figure 9:
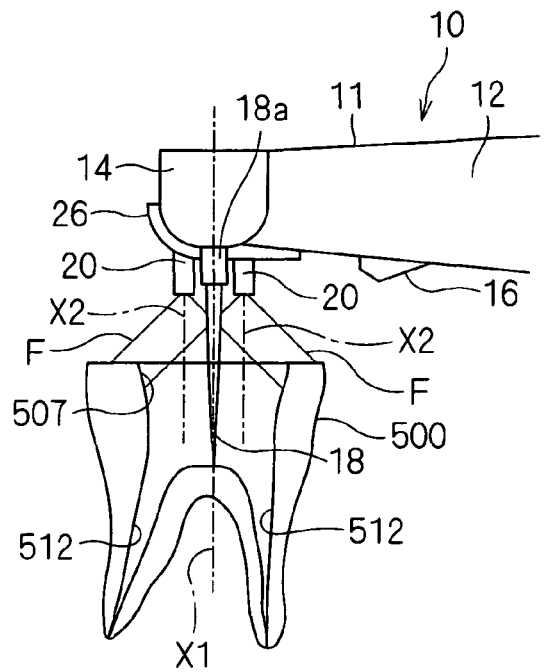
FIG. 9 schematically shows a range of imaging.

FIG. 9 schematically shows the positional relationship between the instrument unit for dental treatment with an imaging device and a root canal during treatment such as root canal enlargement, and a range of imaging by the imaging devices.

As shown in this figure, the head 14 and the imaging modules 20 are placed outside and above the opening of the toot canal 512 when root canal enlargement and imaging of a diseased site are performed by using the instrument unit 10 for dental treatment with an imaging device. Space is generally defined around the rotary cutting tool 18 in the tooth 500 when the rotary cutting tool 18 is placed in the tooth 500. In this condition, the imaging modules 20 perform imaging along the imaging axes X2 substantially parallel to the rotary axis X1 of the rotary cutting tool 18 thereby capturing images of the interior of the tooth 500. So, ranges F of imaging by the imaging modules 20 each include a contact site between the rotary cutting tool 18 and the tooth 500.

Figure 10:
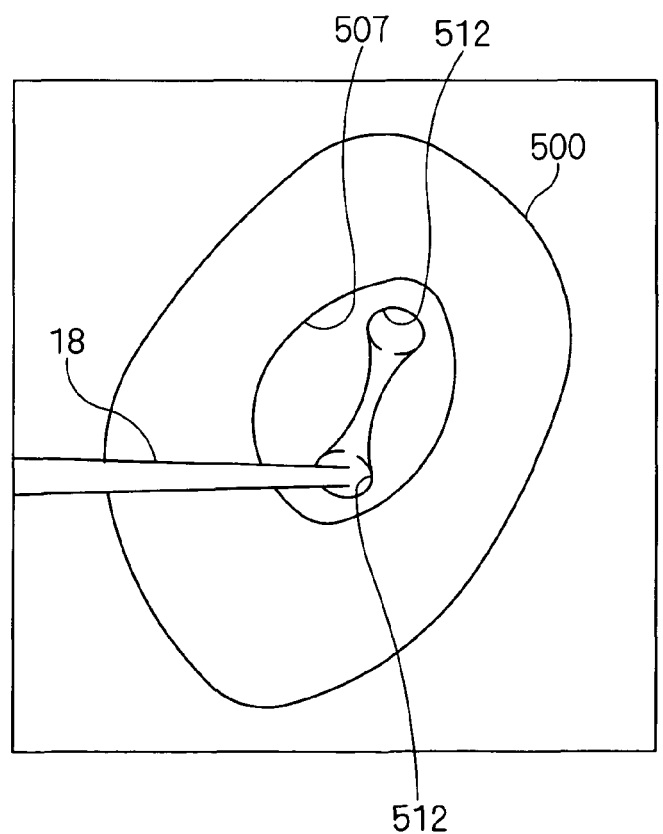
FIG. 10 shows an example of a captured image on a screen.

Thus, images captured by the imaging modules 20 during the root canal enlargement each show a state where the leading end of the rotary cutting tool 18 is placed in the root canal 512 as shown in FIG. 10. These images each include an area inside the tooth 500 that is hard to be viewed directly (see diagonally shaded area in FIG. 2) meaning that an operator can have an image that is originally hard to be viewed directly, especially an image of the interior of the pulp chamber 507 or the root canal 512. If the imaging module is located at a of the illuminating part 16, an image of the interior of the root canal indicated by the diagonal lines in FIG. 2 cannot be captured. In this case, even an image of the leading end of the rotary cutting tool 18 cannot be captured depending on angles. So, the image shown in FIG. 10 cannot be provided.

In the present embodiment, the imaging elements 21 are arranged on the bottom side or the lateral side of the head 14, and the mounting section 26 capable of being attached to and detached from the instrument 11 for dental treatment is provided in order to cause the imaging elements 21 to be attached in their postures that realize the substantially parallel relationship between the imaging axes X2 of the imaging elements 21 and the rotary axis X1 of the rotary cutting tool 18. So, unlike the conventional technique, the present embodiment simplifies a structure while realizing cost reduction by eliminating an expensive image guide. Further, those parts existing around the rotary cutting tool 18 (such as the head 14 or the tooth 500 itself) are unlikely to interfere with imaging of the interior of the pulp chamber 507 or the root canal 512 during the imaging. So, an image of a site being treated including the diagonally shaded area shown in FIG. 2 can more reliably be captured even during the treatment with the rotary cutting tool

18. This, for example, allows an operator to provide treatment while seeing the captured image.

Further, the imaging modules 20 are detachably attached to the instrument 11 for dental treatment. This specific structure allows addition of an imaging function to the instrument 11 for dental treatment that does not originally have an imaging function without making modification, or by making slight modification to the instrument 11 for dental treatment.

The imaging elements 21 can be detached from the head 14. So, the instrument 11 for dental treatment can be subjected to a sterilization process and the like with the imaging elements 21 detached therefrom, thereby preventing a damage to be caused to the imaging elements 21 by the sterilization process.

Further, as a result of the provision of the multiple imaging elements 21, an image of a site being treated is captured from each of the multiple imaging elements 21. So, ranges of imaging by the imaging elements complement each other, by which an operator is given an image of a site being treated that has been captured more reliably.

More specifically, when one imaging element 21 is arranged on the bottom side or the lateral side of the head 14, part of a site being treated may be in a blind spot by the tooth 500 itself and the like depending on the position of the head 14 relative to the tooth 500. In contrast, by the provision of the multiple imaging elements 21 in their respective positions around the rotary cutting tool 18, images captured from different directions are obtained. The extent of an invisible area is reduced by selectively displaying these images, by displaying them at the same time, or by another way.

In the present embodiment, the multiple imaging elements 21 are attached through one mounting section 26. The multiple imaging elements 21 may alternatively be attached through respective mounting sections to the head 14.

The imaging elements 21 are covered with the lens barrels 22. Thus, the resistance to water, the resistance to moisture and the resistance to autoclaving of the imaging elements 21 are enhanced.

Various modifications are described next based on the aforementioned embodiment. In the description given below, the same constituent elements as those previously mentioned are identified by the same reference numerals, and are not described again.

Figure 11:
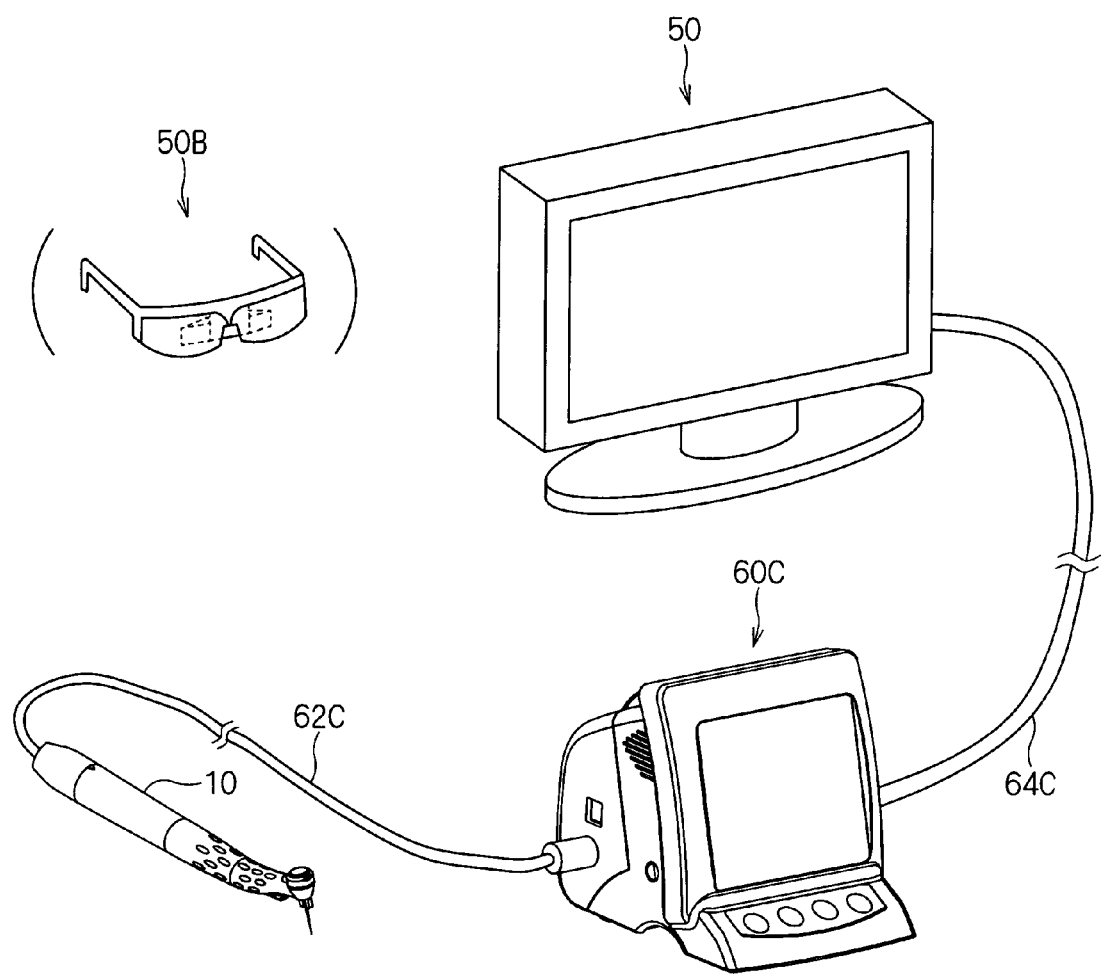
FIG. 11 is an explanatory view of a modification of the imaging and treatment system.

FIG. 11 shows a modification of an exemplary structure of the imaging and treatment system. In this modification, the functions of both the imaging control unit 30 and the instrument control unit 60 described in the first embodiment are incorporated into an instrument control unit 60C. The instrument unit 10 for dental treatment with an imaging device and the instrument control unit 60C are connected to each other through a cable 62C with a drive line for the instrument 11 for dental treatment, and a drive line and an image signal output line for the imaging element 21. Further, the instrument control unit 60C and the display unit 50 are connected to each other through a cable 64C with an image signal output line.

In this modification, the imaging control unit 30 and the instrument control unit 60 of the aforementioned embodiment are physically integrated into one unit, and the number of cables 62C extending from the instrument unit 10 for dental treatment with an imaging device is reduced. Thus, convenience of handling by an operator is enhanced.

Next, two examples of an interconnect line electrically connected to the imaging element 21 are described.

Figure 12:
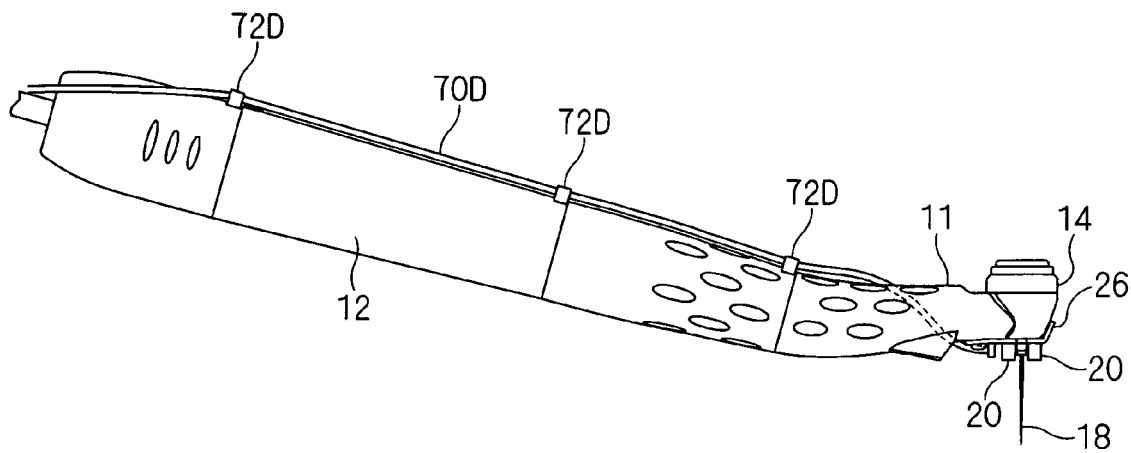
FIG. 12 is a side view of an exemplary interconnect line in the instrument unit for dental treatment with an imaging device.
Figure 13:
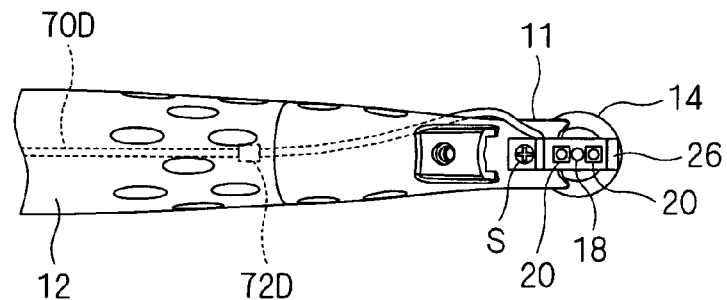
FIG. 13 is a bottom plan view of the exemplary interconnect line in the instrument unit for dental treatment with an imaging device.
Figure 14:
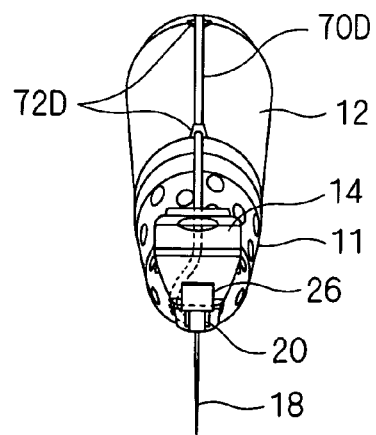
FIG. 14 is a front view of the exemplary interconnect line in the instrument unit for dental treatment with an imaging device.

First, a modification using an external interconnect line 70D is described with reference to FIGS. 12 to 14. This modification includes multiple interconnect line holders 72D provided to the instrument body 12 of the instrument 11 for dental treatment and arranged in the longitudinal direction of the instrument body 12. The interconnect line holders 72D have clamping sections with which the linear interconnect line 70D is held in a way that allows the interconnect line 70D to be attached and detached. The interconnect line holders 72D are attached with an adhesive agent, with a screw, with an engaging mechanism, with a screw, with a fitting mechanism and the like to the instrument body 2 at the outer circumference thereof.

The interconnect line 70D with drive lines and image output lines for the imaging elements 21 is drawn out of the imaging elements 21 to the outside and is detachably attached along the outer circumference of the instrument body 12, in a position held by the interconnect line holders 72D.

Figure 15:
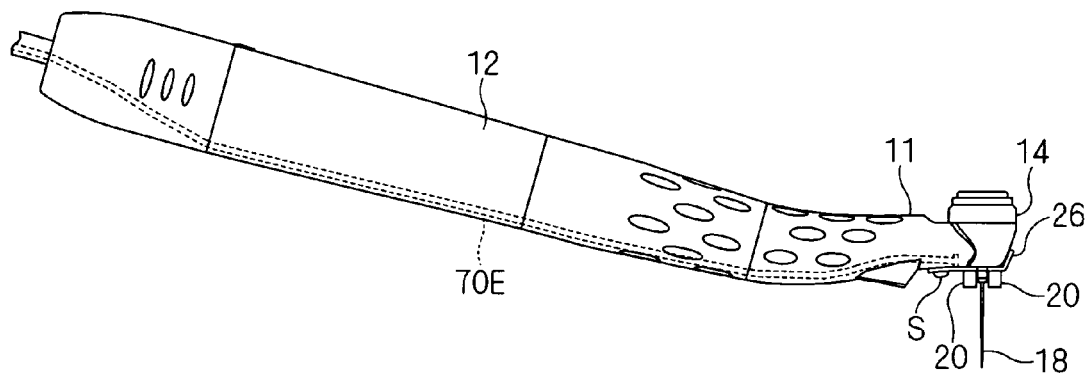
FIG. 15 is a side view of a different exemplary interconnect line in the instrument unit for dental treatment with an imaging device.
Figure 16:
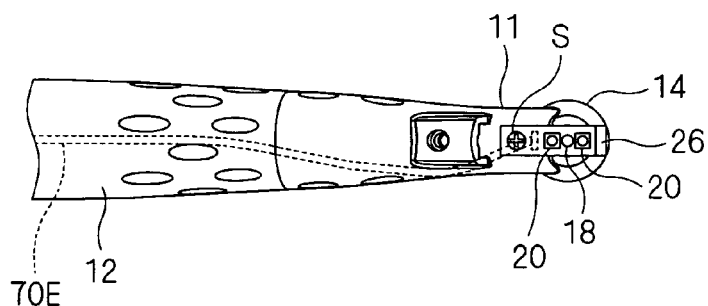
FIG. 16 is a bottom plan view of the different exemplary interconnect line in the instrument unit for dental treatment with an imaging device.
Figure 17:
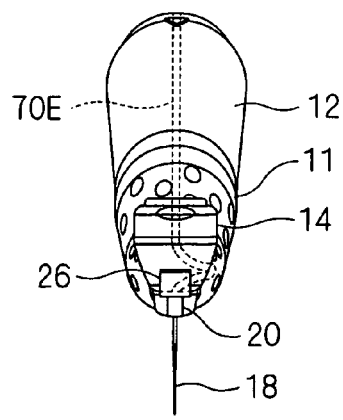
FIG. 17 is a front view of the different exemplary interconnect line in the instrument unit for dental treatment with an imaging device.
Figure 18:
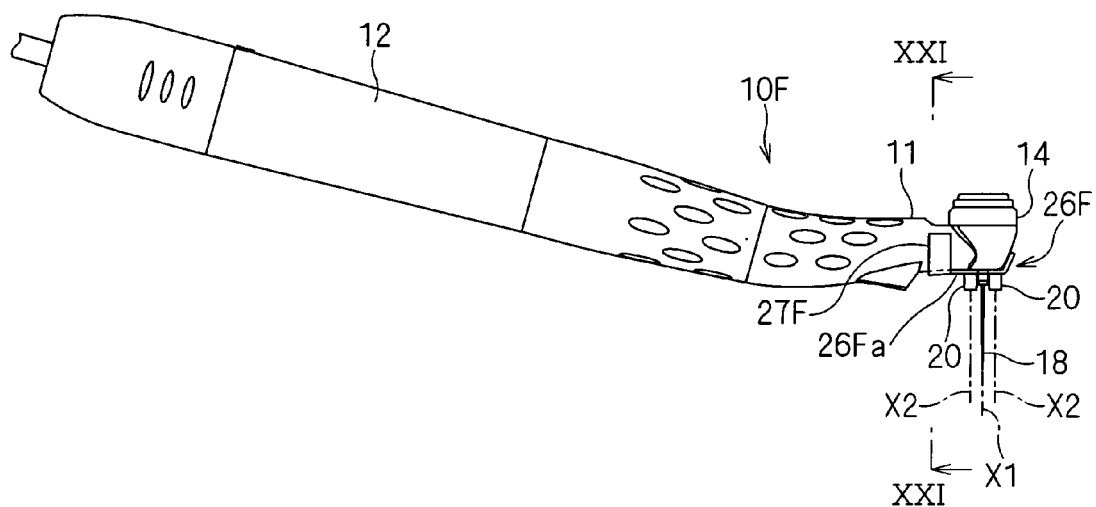
FIG. 18 is a side view of a modification of a mounting section.
Figure 19:
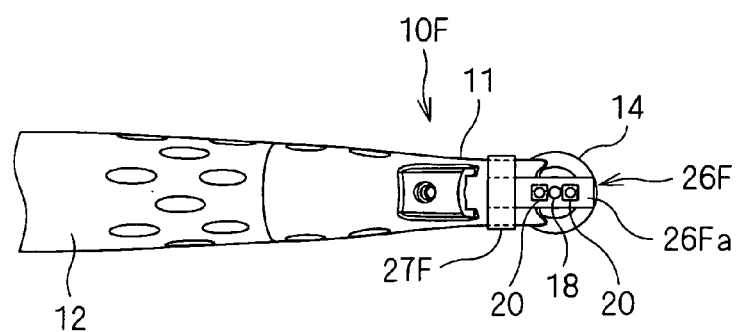
FIG. 19 is a bottom plan view of the modification of the mounting section.
Figure 20:
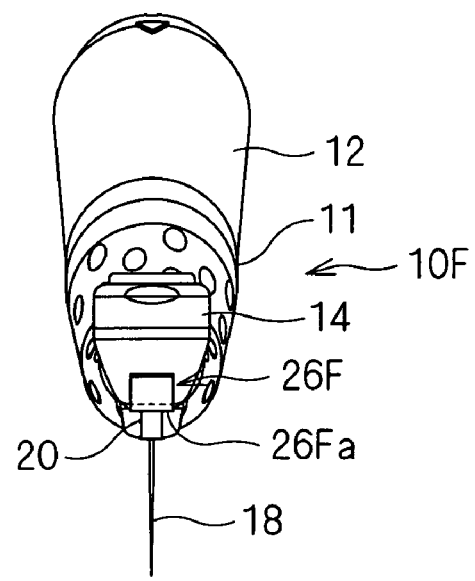
FIG. 20 is a front view of the modification of the mounting section.
Figure 21:
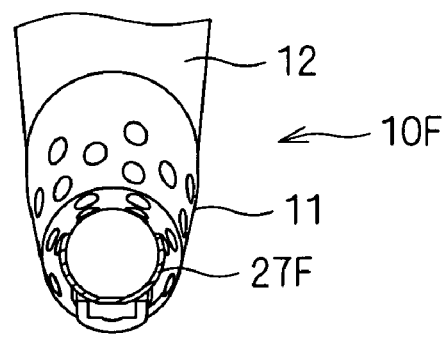
FIG. 21 is a sectional view of the modification of the mounting section taken along a line XXI-XXI.

Next, a modification using a buried interconnect line 70E is described with reference to FIGS. 15 to 17. In this modification, the interconnect line 70E with drive lines and image output lines for the imaging elements 21 is buried in the instrument body 12, while extending in the longitudinal direction of the instrument body 12. The provision of the interconnect line 70E inside the instrument body 12 includes for example a case where the interconnect line 70E is placed along the inner circumference of an outer case of the instrument body 12.

These modifications allow the imaging elements 21 to be electrically connected to an external device through the interconnect line 70D detachably attached along the outer circumference of the instrument body 12, or through the interconnect line 70E provided inside the instrument body 12. With reference especially to the former modification, it allows attachment and detachment of the interconnect line 70D together with the imaging elements 21. So, the instrument 11 for dental treatment is subjected to a sterilization process and the like with the interconnect line 70D and the imaging elements 21 detached therefrom. This prevents a damage to be caused to the imaging elements 21 and the interconnect line 70D by the sterilization process and the like. The former modification also allows the interconnect line 70D to be added in a relatively easy way to the already-existing instrument 11 for dental treatment. The latter modification avoids exposure of the interconnect line 70E to the outer circumference of the instrument body 12, thereby achieving excellent convenience of handling by an operator.

Described next is a modification of the mounting section 26 through which the imaging module 20 is detachably attached.

FIGS. 18 to 21 show how the present invention, is put into practice using a mounting section 26F of the modification. An instrument unit 10F for dental treatment with an imaging device of this modification uses the mounting section 26F instead of the above-mentioned mounting section 26. The mounting section 26F is made of resin and the like, and has a module fixing portion 26Fa and a fitting portion 27F. Of course, the mounting section 26F as a whole may function as a board. The module fixing portion 26Fa has the same structure as that of the mounding section 26, with the exception that the module fixing portion 26Fa does not have a structure for screw fixation. The fitting portion 27F is integrally provided to the module fixing portion 26Fa, at an end portion of the module fixing portion 26Fa on the side with respect to the instrument body 12. The fixation of the fitting portion 27F to the imaging modules 20 or to the imaging elements 21 through a different member such as the module fixing portion 26Fa is also regarded as one of ways of fixing the fitting portion 27F to the imaging modules 20 or to the imaging elements 21. In the figures, the fitting portion 27F is approximately in a C-shape that allows the fitting portion 27F to be elastically fitted into a portion of the instrument body 12 near the head 14.

The portion of the instrument body 12 near the head 14 is placed in the fitting portion 27F with the opening of the fitting portion 27F widened, and thereafter, the fitting portion 27F is caused to elastically return to its original form. As a result, the module fixing portion 26Fa is placed at one end portion of the head 14. At the same time, with the imaging modules 20 placed around the rotary cutting tool 18, the mounting section 26F is attached to the instrument 11 for dental treatment in such a way that it is elastically fitted onto the instrument 11 for dental treatment. When the opening of the fitting portion 27F is widened in this state in order for the portion of the instrument body 12 near the head 14 to be pulled out of the fitting portion 27F, the mounting section 26F is detached from the instrument 11 for dental treatment.

The mounting section 26F advantageously allows the imaging modules 20 to be detachably attached easily without adding processing such as formation of a screw hole to the instrument 11 for dental treatment. Further, the imaging modules 20 are attached and detached in a relatively easy way.

In the aforementioned modification, the fitting portion is an elastic fitting portion that can easily be attached to and detached from the instrument 11 for dental treatment. According to an example of this structure, an elastic member approximately in a C-shape is detachably attached to the outer circumference of the head 14. According to another example, an elastic member approximately in a ring shape or a closed-end cylindrical shape is fitted from outside to one end portion or to the opposite end portion of the head 14, and the elastic member can be attached to and detached from the head 14 by a fastening force generated by the elastic restoring force of the elastic member and by a frictional force against the head 14. The elastic fitting is not the only exemplary way of fitting, but various fitting ways are applicable. As an example, a recess to be fitted to a projection of the head may be defined in the fitting portion, and the recess and the projection may be fitted together (not shown).

The structure of the mounting section that can be attached to and detached from the instrument 11 for dental treatment is not limited to that described above. They mounting section may have a pawl. In this case, the mounting section is allowed to be attached to and detached from the instrument 11 for dental treatment by the engagement formed between the pawl and a predetermined site of the head 14 (such as a recess defined in the outer circumference thereof). Or, the aforementioned structures may be applied in combination. The point is that, as long as the imaging modules 20 and the imaging elements 21 can be attached to and detached from the instrument 11 for dental treatment while kept in their positions and postures described above, the mounting section may be of any structure.

Second Embodiment

An instrument unit for dental treatment with an imaging device of a second embodiment is described next. In the second embodiment, an illuminating part for applying light used for imaging is detachably attached. The same constituent elements as those mentioned in the first embodiment are identified by the same reference numerals, and are not described again.

Figure 22:
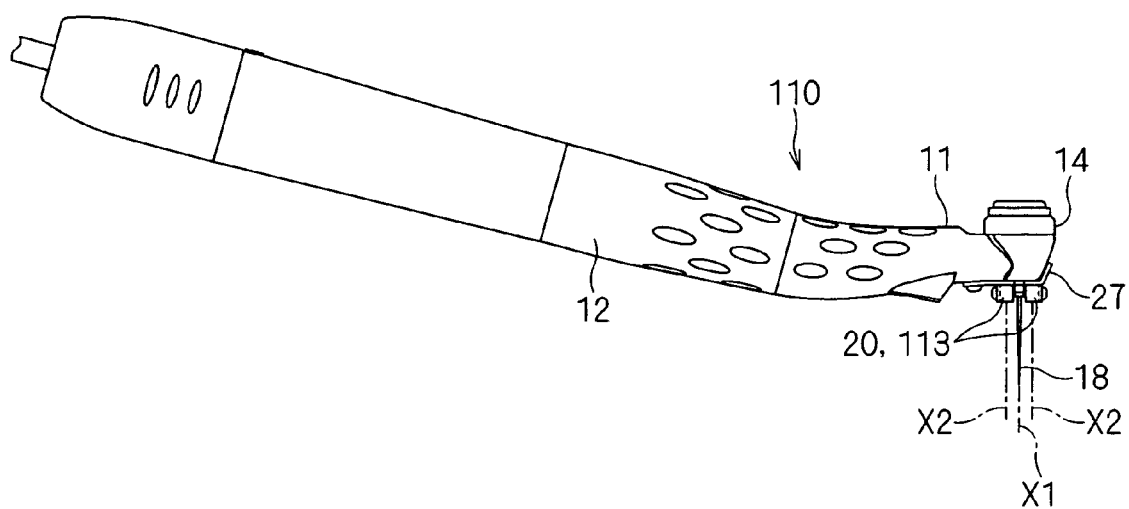
FIG. 22 is a side view of an instrument unit for dental treatment with an imaging device according to a second embodiment of the present invention.
Figure 23:
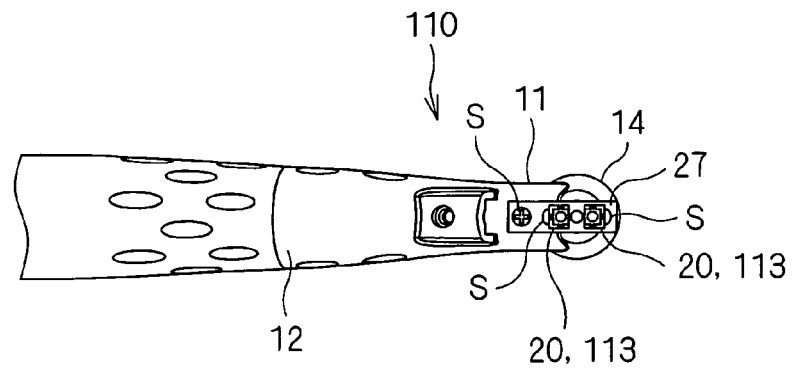
FIG. 23 is a bottom plan view of this instrument unit for dental treatment with an imaging device.
Figure 24:
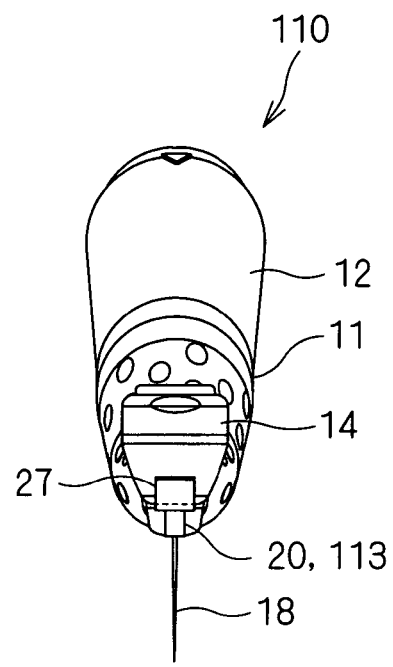
FIG. 24 is a front view of this instrument unit for dental treatment with an imaging device.
Figure 25:
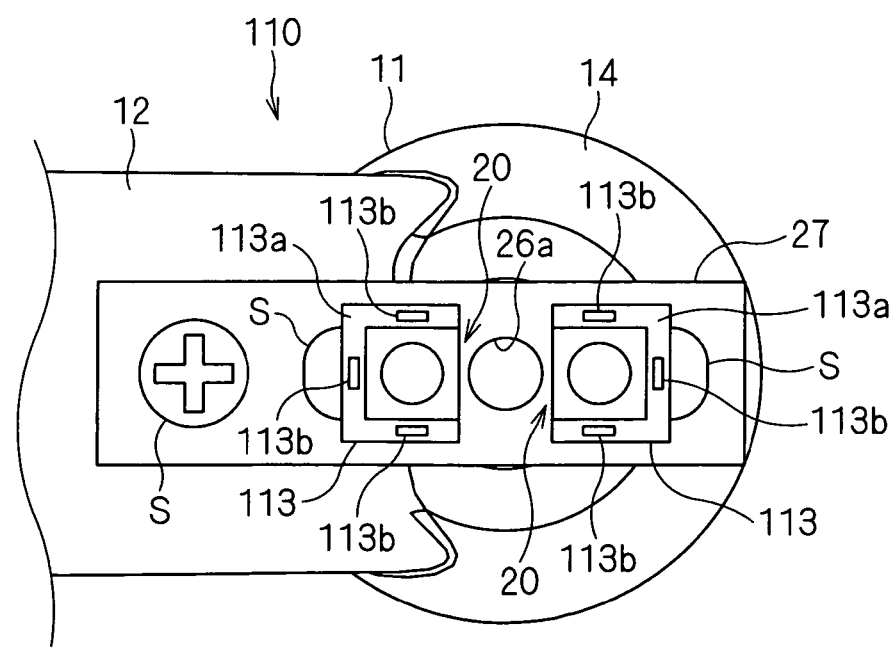
FIG. 25 is an enlarged bottom plan view of this instrument unit for dental treatment with an imaging device.

Illuminating parts 113b detachably attached through the imaging modules 20 are described first. FIGS. 22 to 24 are a side view, a bottom plan view, and a front view of an instrument unit 110 for dental treatment with an imaging device according to the second embodiment. FIG. 25 is an enlarged view of the imaging modules 20 and their vicinities of the instrument unit 110 for dental treatment with an imaging device.

In the imaging modules 20 and their vicinities of the instrument unit 110 for dental treatment with an imaging device, illumination modules 113 are detachably attached to the imaging modules 20, so that the illuminating parts 113b are detachably attached to the bottom side or the lateral side (here, to the bottom side) of the head 14.

More specifically, the illumination modules 113 each include a bracket 113a and the illuminating parts 113b functioning as light emitters for illumination purpose.

The brackets 113a are each made of resin and the like, and is formed into a shape that allows detachable attachment to the outer circumference of the imaging module 20. The bracket 113a is a member approximately in a U-shape in appearance, with opposite ends of a coupling side, and two lateral sides extending from the opposite ends of the coupling side in postures substantially vertical to the coupling side. The shape of the bracket 113a is such that it allows the bracket 113a to be detachably attached from outside, in such a way as to surround three outer sides of the imaging module 20. Like the lens barrel 22, the bracket 113a is preferably made of heat-resistant resin. This is because, as it allows the illuminating parts 113b to be covered with the bracket 113a as a protective member made of heat-resistant resin, resistance to water, resistance to moisture and resistance to autoclaving are enhanced.

The illuminating parts 113b are each constructed of a light-emitting element such a light-emitting diode, an electroluminescence element or the like, and are buried in the coupling side and each lateral side of the bracket 113a, in such a way that the illuminating parts 113b can emit light to the outside. It is preferable that the illuminating parts 113b emit light in a direction substantially parallel to that of the aforementioned rotary axis X1. Further, the illuminating parts 113b and the imaging axes X2 (see FIG. 22) are preferably as close as possible.

A screw clearance hole is defined in the coupling side of each bracket 113a, and a screw fixing hole is defined in one lateral side of the corresponding imaging module 20. With the bracket 113a fitted from outside onto the outer circumference of the imaging module 20, a screw S is driven through the screw clearance hole into the screw fixing hole. As a result, the illumination modules 113 each including the illuminating parts 113b are detachably attached to the bottom side of the head 14. That is, the detachable attachment of the illuminating parts 113b to the bottom side of the head 14 includes the case where the illuminating parts 113b are attached through a different member (here, imaging modules 20). A wiring pattern for conduction may be provided to each bracket 113a instead of the board 25 inside the imaging module. In this case, electrical connection is established between the wiring pattern, and the imaging module and the illumination module, namely the bracket 113a itself is regarded as an electric circuit board. Further, a conductive circuit is formed by placing the imaging module and the illumination module onto the bracket 113a having a function of a board.

Multiple (here, two) imaging modules 20 are provided. So, the imaging modules 113 are detachably attached to the corresponding imaging modules 20.

Figure 26:
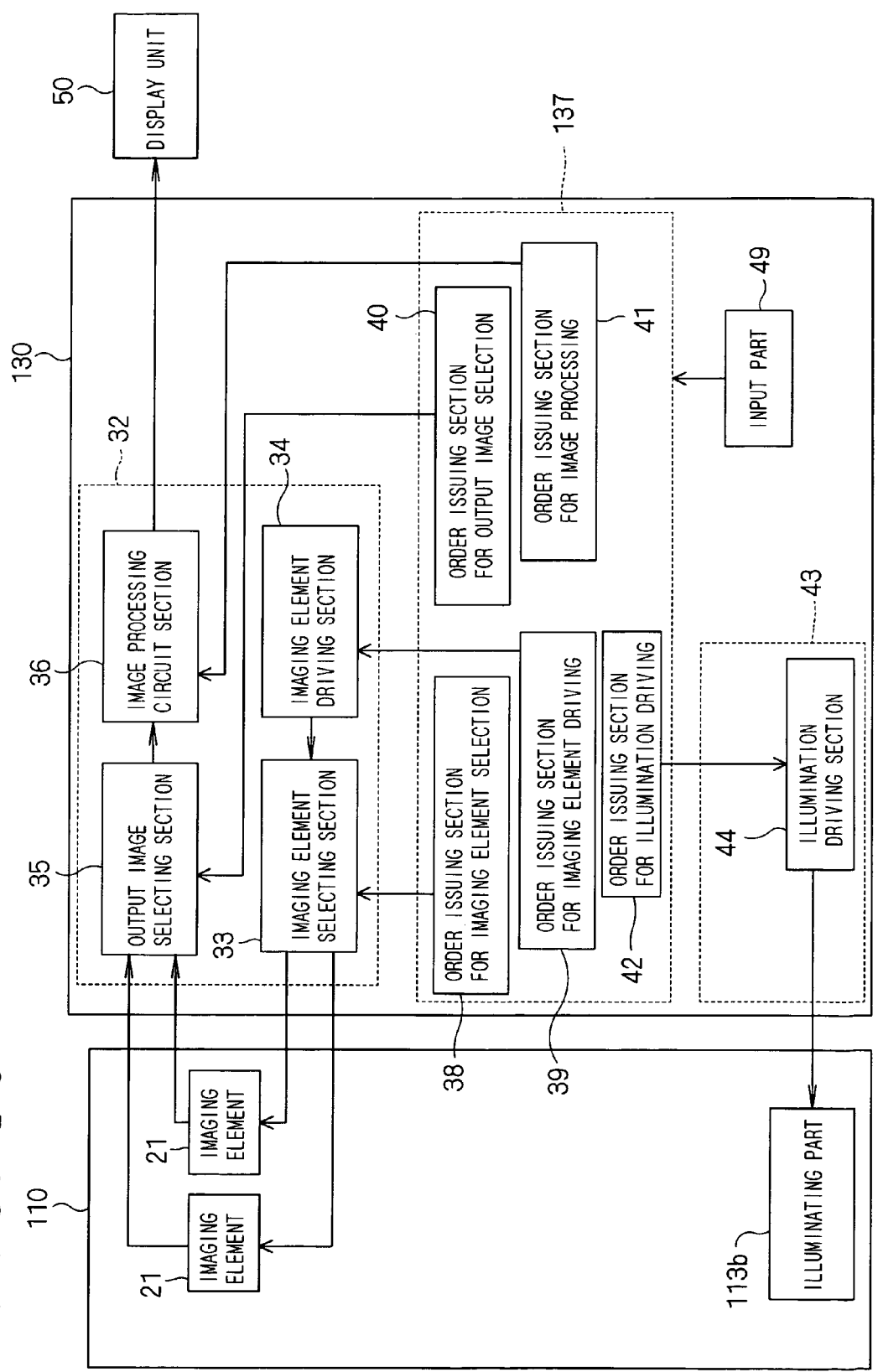
FIG. 26 is a block diagram including this instrument unit for dental treatment with an imaging device, an imaging control unit, and a display unit.

FIG. 26 is a block diagram including the instrument unit 110 for dental treatment with an imaging device, an imaging control unit 130, and the display unit 50 of the second embodiment.

This block diagram differs from the block diagram of the first embodiment shown in FIG. 8 in that, the imaging control unit 130 further includes an illumination control part 43 with an illumination driving section 44, and that a control order issuing part 137 has the function of an order issuing section 42 for illumination driving.

The function of the order issuing section 42 for illumination driving is realized for example as a processing function of the control order issuing part 37. The illumination driving section 44 is constructed of a driving circuit and the like for the illuminating parts 113*b*, and is connected through a cable and the like to the illuminating parts 113*b*.

The order issuing section 42 for illumination driving issues a driving order to the illumination driving section 44 at a time when one of the imaging elements 21 is to perform imaging. After receiving the driving order, the illumination driving section 44 outputs a driving signal for driving the illuminating part 113*b*, in response to which this illuminating part 113*b* emits light.

All the illuminating parts 113*b* may be caused to emit light regardless of which one of the imaging modules 20 is to perform imaging. Or, illumination by the illuminating parts 113*b* may independently be controlled for each illumination module 113. In this case, when one of the imaging modules 20 is to perform imaging, only the illuminating parts 113*b* of the illumination module 113 attached to this imaging module 20 responsible for the imaging are caused to emit light.

According to the aforementioned structure of the instrument unit 110 for dental treatment with an imaging device, the imaging elements 21 are allowed to perform imaging while a site being treated and the like are lighted up by the illuminating parts 113*b*. As a result, an image more suitably applicable for treatment is obtained.

In order to realize detachable attachment of the illuminating parts 113*b*, the imaging modules 20 are placed on a board or a bracket having the function of a board, and the board or the bracket having the function of a board is formed into a shape that allows attachment and detachment thereof. In addition to this structure, alternative structures including those that use the screw S, an elastic member approximately in a C-shape, an elastic member approximately in a ring shape or approximately in a closed-end cylindrical shape, a pawl, and a projection (or a recess) fitted to a recess (or a projection) defined in the outer circumference of the imaging module, are applicable. Still alternatively, the illuminating parts 113*b* may be attached to the instrument 11 for dental treatment, for example to the head 14. The point is that, as long as the illuminating parts 113*b* can be attached to and detached from the instrument 11 for dental treatment while the illumination modules 1113 are kept in their predetermined positions, any structure is applicable.

Various modifications are described next based on the aforementioned embodiment. In the description given below, the same constituent elements as those previously mentioned are identified by the same reference numerals, and are not described again.

Figure 27:
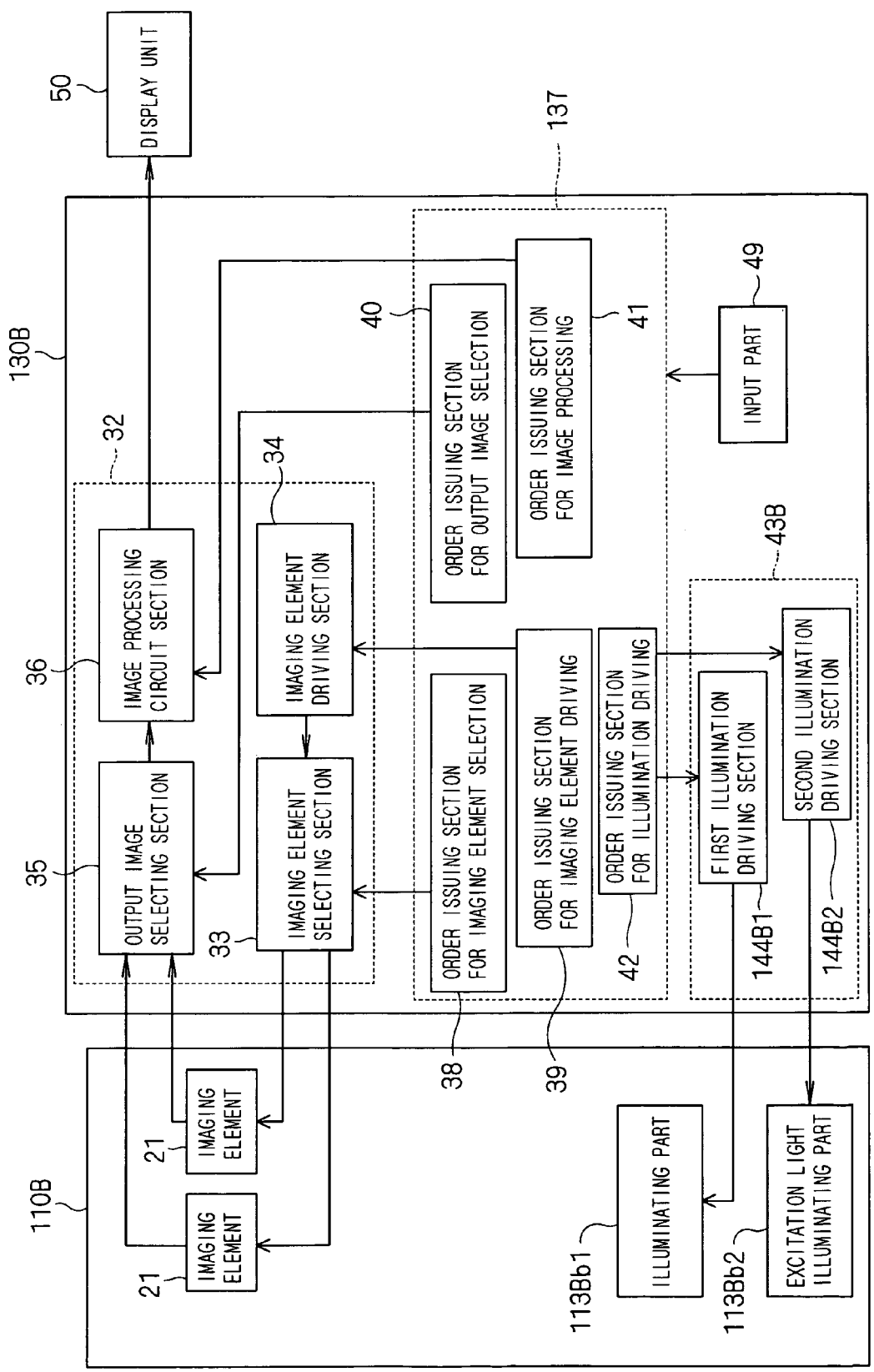
FIG. 27 is a block diagram of a modification in which multiple illuminating parts are provided.

First, the illuminating parts 113*b* provided in each illumination module 113 may include an illuminating part for normal imaging, and an excitation light illuminating part for use in a fluorescent image for extracting an abnormal site. FIG. 27 is a block diagram according to this modification.

The block diagram of FIG. 27 mainly differs from the block diagram of FIG. 26 in that, an instrument unit 110B for dental treatment with an imaging device includes an illuminating part 113Bb1 for normal imaging and an excitation light illuminating part 113Bb2 for use in a fluorescent image for extracting an abnormal site, and that an illumination control part 43B of an imaging control unit 130B includes a first illumination driving section 144B1 for the illuminating part 113Bb1, and a second illumination driving section 144B2 for the excitation light illuminating part 113Bb2.

The illuminating part 113Bb1 emits light in a visible light range, and is constructed of a white diode and the like. The excitation light illuminating part 113Bb2 emits light of a wavelength for example of 405 nm, and is constructed of a light-emitting diode and the like. Irradiation with light of this wavelength causes emission of red fluorescence or orange fluorescence from an abnormal site such as dental tartar, tooth plaque or softened dentin. So, receipt of this fluorescence allows the fluorescence emitted from the abnormal site to be extracted visually, thereby allowing the imaging element 21 to capture an image including the extracted abnormal site. A filter for cutting out excitation light such as that for cutting out a wavelength component of not greater than 430 nm is preferably arranged ahead of the imaging element 21 when an image of an abnormal site extracted by the excitation light illuminating part 113Bb2 is to be captured. When excitation light is not cut out, all wavelength regions enter the imaging element 21. This causes the color of an excited abnormal site to be buried in an excitation light component, thereby making recognition of the abnormal site difficult. This is the reason for the provision of a filter, and an example of which is described later.

After receiving instructions for illumination by either the illuminating part 113Bb1 or the excitation light illuminating part 113Bb2, or by both of them that have been given through the input part 49, the control order issuing part 137 issues an order for illumination driving to either the first illumination driving section 144B1 or the second illumination driving section 144B2, or to both of them in response to the instructions. Then, either the first illumination driving section 144B1 or the second illumination driving section 144B2, or both of them, outputs driving signals to the illuminating part 113Bb1 and the excitation light illuminating part 113Bb2 corresponding thereto. In response, the illuminating part 113Bb1 and the excitation light illuminating part 113Bb2 emit light selectively, or at the same time.

This allows imaging accompanied by emission of light that is responsive to the needs of the imaging.

Figure 28:
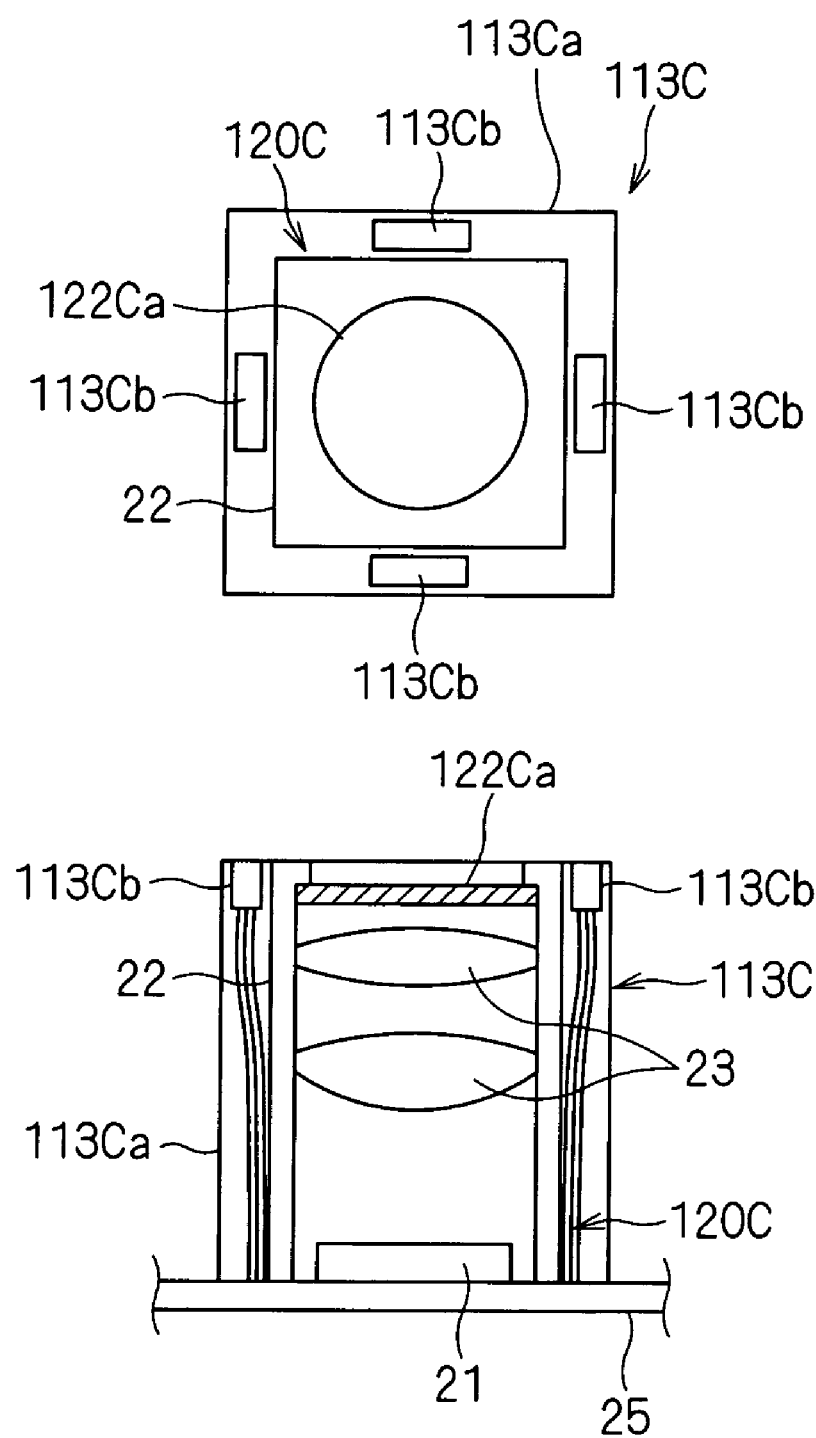
FIG. 28 shows an imaging module and an illumination module according to a modification.

FIG. 28 shows an imaging module 120C and an illumination module 113C according to a modification.

In this modification, the illumination module 113C has a bracket 113Ca approximately in a rectangular cylindrical shape that can be fitted from outside to the imaging module 120C. Four illuminating parts 113Cb are provided in such a way as to surround the four sides of the bracket 113Ca. The illuminating parts 113Cb include an illuminating part for normal imaging, and an excitation light illuminating part for use in a fluorescent image for extracting an abnormal site. The illuminating parts 113Cb are connected through an interconnect line inside the bracket 113Ca to the board 25.

The imaging module 120C includes a filter 122Ca arranged in the lens barrel 22 approximately in a rectangular cylindrical shape. The filter 122Ca is capable of cutting out the aforementioned excitation light. Instead of providing the filter 122Ca separately, the filter 122Ca is required to be located closer to a target of imaging than the imaging element 21. The lens 23 may be covered with a coating having a function of a filter capable of cutting out excitation light.

This allows formation of an image in which an abnormal site excited by excitation light is easily recognized.

Figure 29:
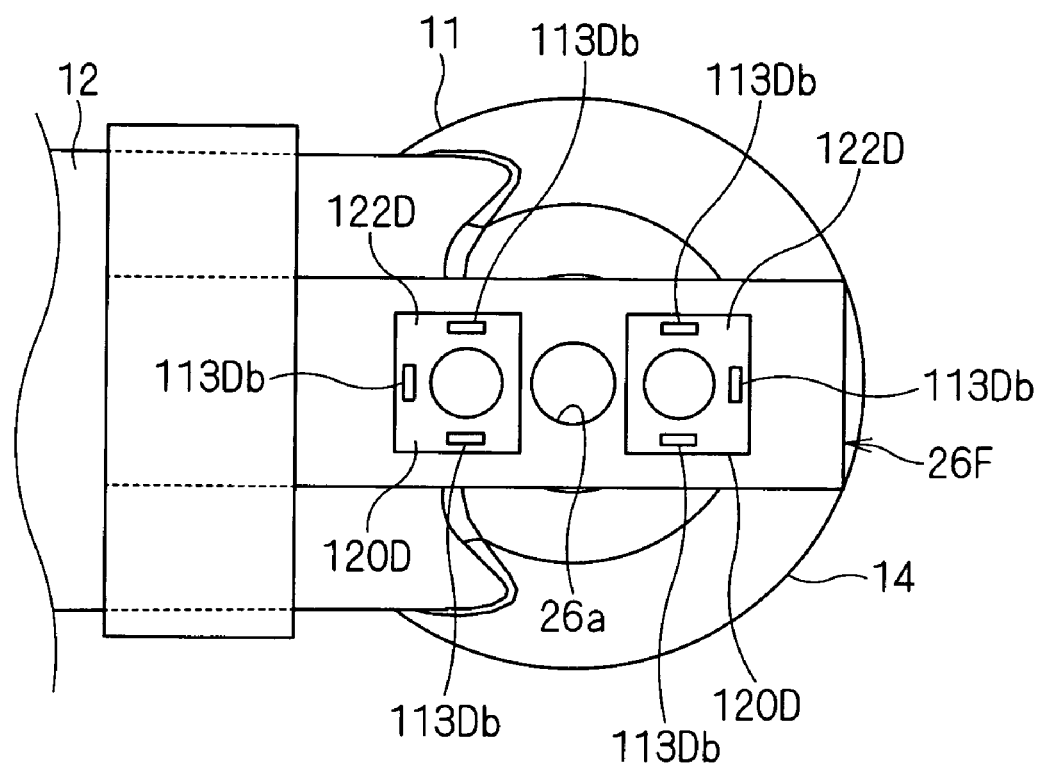
FIG. 29 is an enlarged bottom plan view of a modification in which an imaging element and illuminating parts are unified to form an imaging module.

In the structure according to a modification shown in FIG. 29, each of the imaging elements 21 and illuminating parts 113Db are integrated into one as an imaging module 120D.

More specifically, a total of three illuminating parts 113Db are arranged on three sides of the perimeter of each of lens barrels 122D corresponding to the lens barrel 22. In order to incorporate the illuminating parts 113Db into the lens barrels 122D, the illuminating parts 113Db may be fitted into recesses defined in the lens barrels 122D. Alternatively, the illuminating parts 113Db may be insert-molded into the lens barrel 122D.

According to this modification, each of the imaging elements 21 and the illuminating parts 113b as one unit can easily be attached to and detached from the instrument 11 for dental treatment, thereby providing excellent maintainability. Further, each of the imaging elements 21 and the illuminating parts 113b are protected by the lens barrel 122D as one protective member, thereby contributing to the simplification of a structure.

Figure 30:
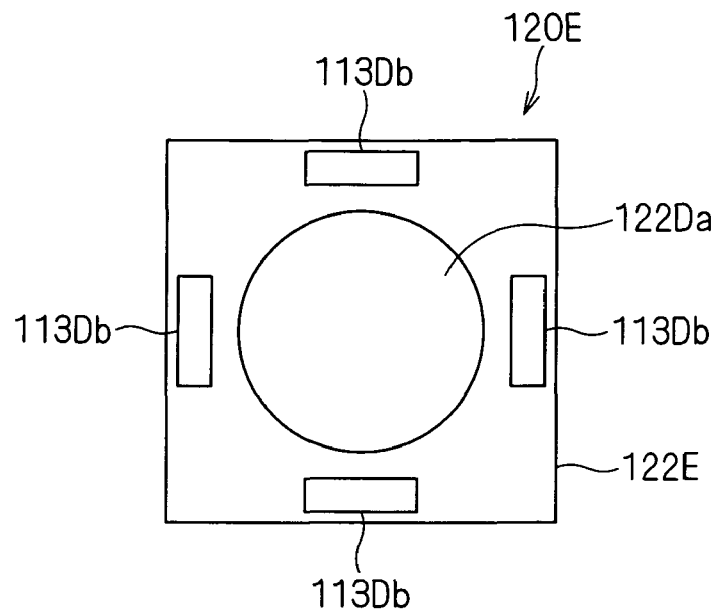
FIG. 30 is a bottom plan view of a modification of an imaging module.
Figure 31:
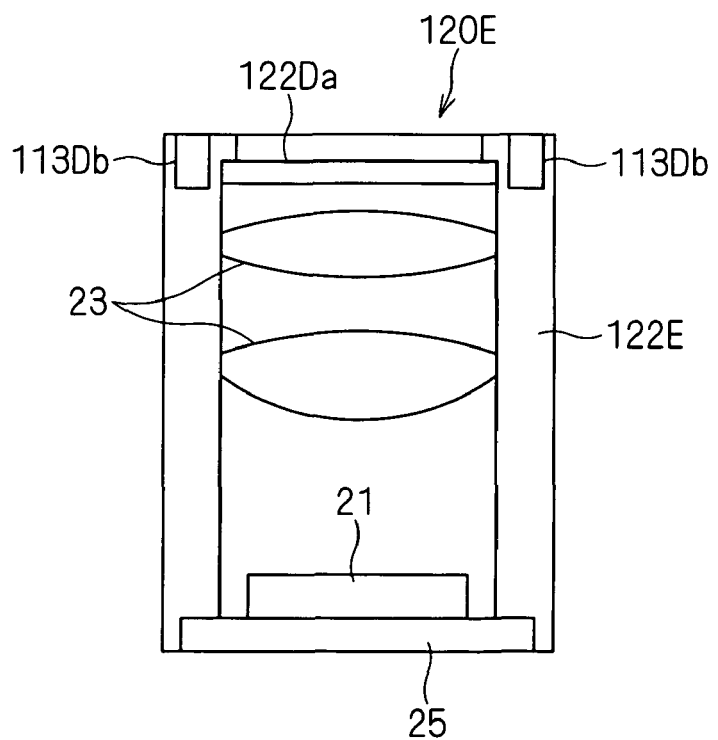
FIG. 31 is a sectional view of the modification of the imaging module.
Figure 33:
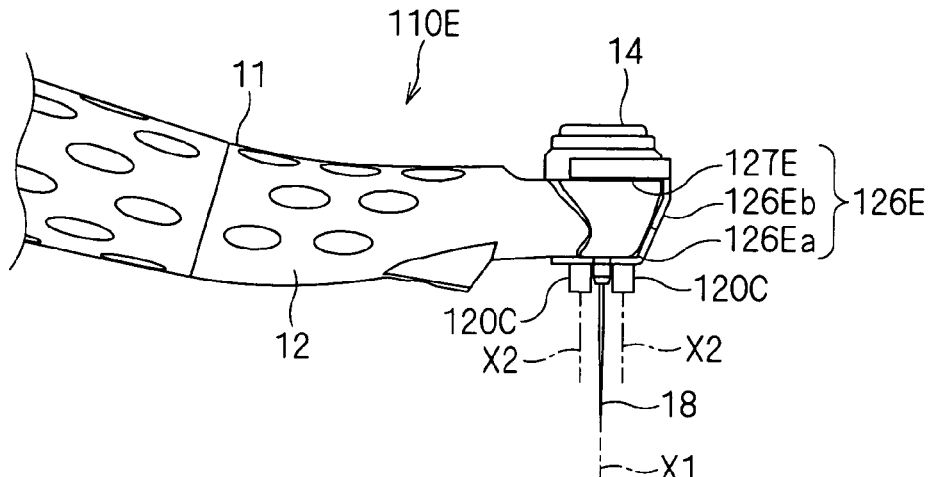
FIG. 33 is a side view of an instrument unit for dental treatment with an imaging module according to a modification.
Figure 34:
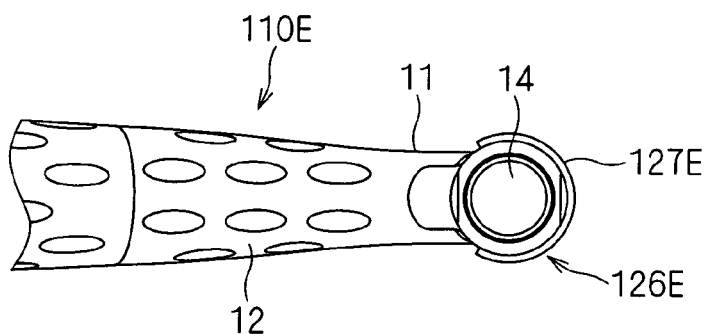
FIG. 34 is a top plan view of the instrument unit for dental treatment with an imaging module according to the modification.
Figure 35:
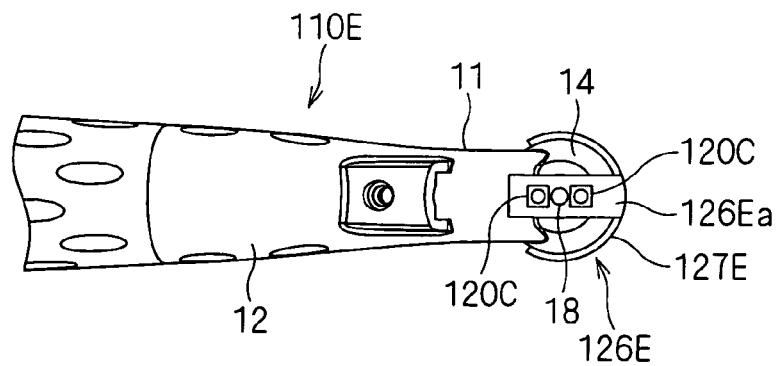
FIG. 35 is a bottom plan view of the instrument unit for dental treatment with an imaging module according to the modification.
Figure 36:
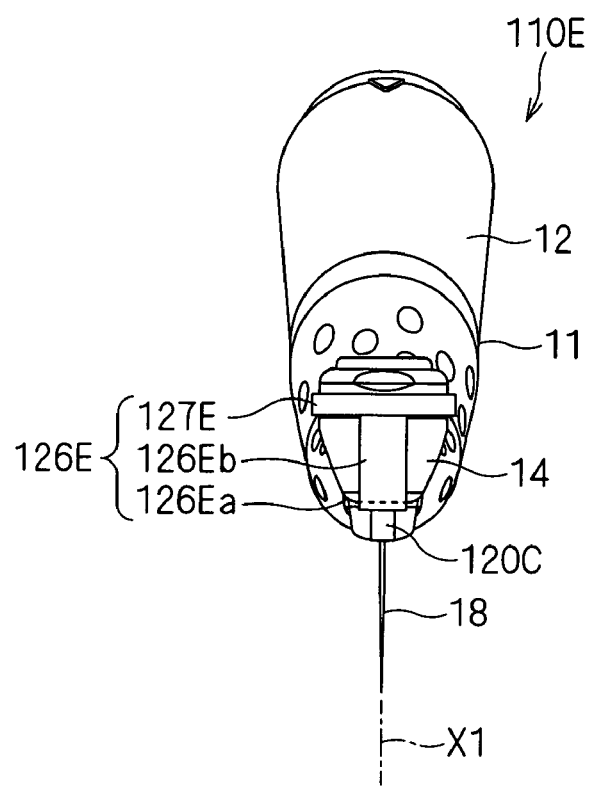
FIG. 36 is a front view of the instrument, unit for dental treatment with an imaging module according to the modification.

In a modification shown in FIGS. 30 and 31, a total of four illuminating parts 113Db are arranged on four sides of the perimeter of a lens barrel 122E corresponding to the lens barrel 22 to form an imaging module 120E.

A filter 122Da functioning in the same manner as the filter 122Ca is provided in the lens barrel 122E.

A contact area of an opening of the lens barrel 122E with the board 25 or with the filter 122Da preferably has a sealing structure. This sealing structure may be realized for example by a structure in which adhesion is given with an adhesive agent or in which a sealing member such as an O-ring is used, or by a structure in which the lens barrel 122E is formed by molding together with the board 25 and the filter 122Da as objects to be insert molded.

In the example shown in FIG. 32, an outer case 122Ea is formed by molding together with the lens barrel 122E and the board 25 as objects to be insert molded, in such a way as to cover the outer circumference of the lens barrel 122E and the board 25. This more reliably seals space between the opening of the lens barrel 122E and the board 25, thereby providing resistance to water and resistance to moisture at higher levels of excellence. Further, instead of providing the board 25, a wiring pattern for conduction may be provided for example to the mounting section 26F shown in FIG. 29, so that the mounting section 26F itself is applicable as a board. In this case, a conductive circuit is formed by placement of the imaging module 120E onto the mounting section 26F.

In a modification described next, the imaging element 21 is provided movably about the head 14.

FIGS. 33, 34, 35 and 36 are a side view, a top plan view, a bottom plan view, and a front view of the head 14 and its vicinity of an instrument unit 110E for dental treatment with an imaging device according to this modification.

The instrument unit 110E for dental treatment with an imaging device includes a mounting section 126E of a structure as follows. The mounting section 126E is made of resin and the like, and has a mounting body portion 126Ea, a fitting portion 127E, and a coupling portion 126Eb.

The mounting body portion 126Ea has the same structure as that of the mounding section 26, with the exception that the mounting body portion 126Ea does not have a structure for screw fixation. The imaging modules 120C are fixed about the rotary axis X1 of the rotary cutting tool 18, in the same manner as the imaging modules 20.

The fitting portion 127E is rotatably fitted on the head 14. More specifically, the fitting portion 127E is an elastic portion approximately in a C-shape, and is rotatably fitted from outside to the upper end portion of the head 14.

The coupling portion 126Eb is formed approximately into an elongated plate for connecting the mounting body portion 126Ea and the fitting portion 127E in a position in the vicinity of the head 14, and which does not overlap a joint portion with the instrument body 12.

Figure 37:
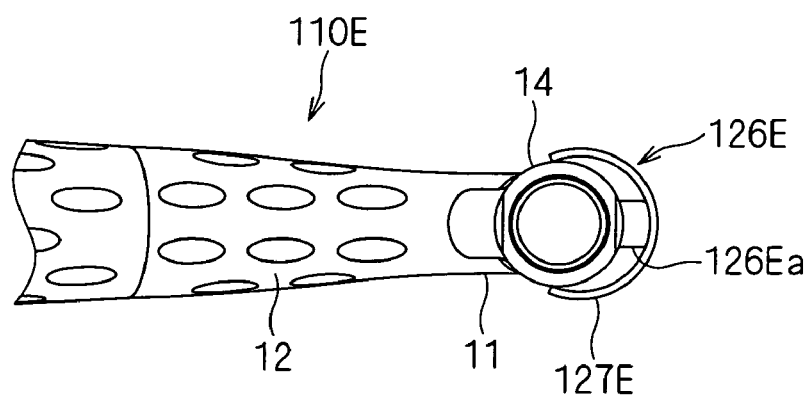
FIG. 37 is an explanatory view of a mounting section on its way of being attached.

The mounting section 126E is attached to the head 14 in the way as follows with the rotary cutting tool 18 detached therefrom. First, the upper end portion of the head 14 is pushed into the opening of the fitting portion 127E as shown in FIG. 37 while the mounting body portion 126Ea is placed on the lower end portion of the head 14. Then, the opening of the fitting portion 127E is widened. After the upper end portion of the head 14 is fitted into the fitting portion 127E, the fitting portion 127E returns to its original form. Then, resultant elastic force causes the fitting portion 127E to be attached to the upper end portion of the head 14, in such a way that the upper end portion of the head 14 is tightened up with the fitting portion 127E. As a result, the mounting section 126E is attached to the head 14, and the imaging modules 120C are placed in the positions relative to the head 14, and in the same postures as those described above.

Figure 38:
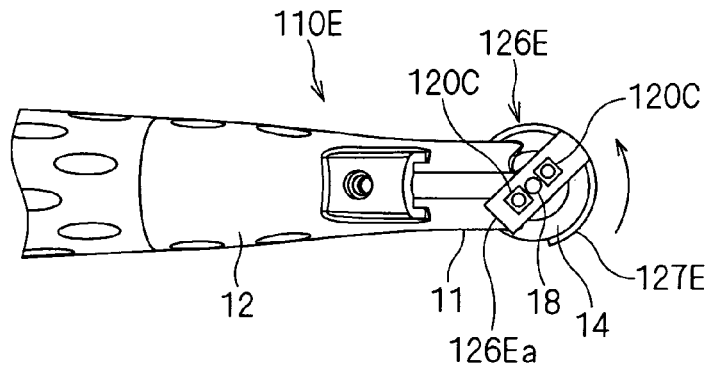
FIGS. 38 and 39 are each an explanatory view showing how a mounting section and imaging modules move.
Figure 39:
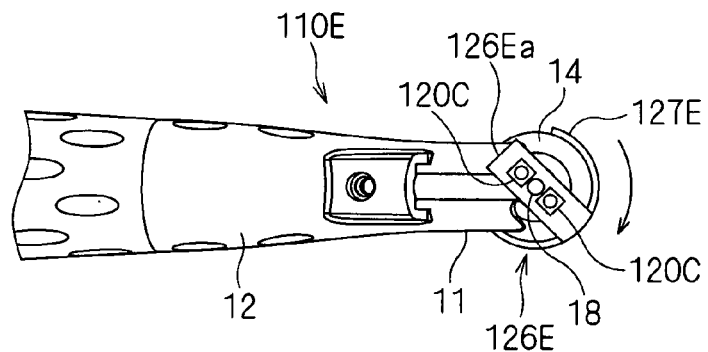

The coupling portion 126Eb in this state is located in a position in the vicinity of the head 14, and on the opposite side of the joint portion with the instrument body 12. Further, the fitting portion 127E is fitted on the head 14 by a fitting force with a strength that allows the fitting portion 127E to rotate about the upper end portion of the head 14 by an operation with fingers. So, by causing the fitting portion 127E to rotate about the upper end portion of the head 14 within a range in which the coupling portion, 126Eb in the vicinity of the head 14 abuts on the joint portion with the instrument body 12, the mounting portion 126E is allowed to rotate about the head 14 as shown in FIGS. 38 and 39. The rotation of the mounting section 126E in this way also allows the imaging modules 120C to rotate about the rotary axis X1. As a result, imaging is performed from various directions around the rotary cutting tool 18. This provides enhanced convenience, while realizing control of imaging direction according for example to the shapes of a site to be treated and its vicinity.

Figure 40:
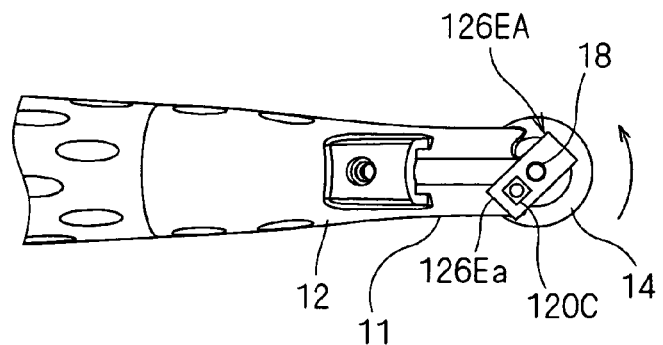
FIG. 40 is an explanatory view showing how a mounting section and an imaging modules move.

The structure for causing the imaging module 120C to rotate about the rotary cutting tool 18 is not necessarily limited to the above-described example. By way of example, like a mounting section 126EA shown in FIG. 40, a fitting section of a shape that allows fitting by applying frictional force generated by a structure with a recess and a projection may be provided to the bottom side of the head 14. Further, the mounting body portion 126Ea may rotatably be attached to the fitting section with a bearing and the like provided near its central portion through which a tool passes, thereby causing the imaging module 120C to rotate about the rotary cutting tool 18 by the rotation of the mounting body portion 126Ea. In this case, the aforementioned rotatable structure is realized by the fitting section that does not employ elastic deformation. The rotation may be made by directly touching the mounting body portion 126Ea with fingers, or by holding a lever and the like not shown provided to the mounting body portion 126Ea. While only one imaging module 120C is shown in FIG. 40, multiple imaging modules may be provided. As another example, a mounting section in the form of a cap may elastically and rotatably be attached from outside to the bottom side of the head 14. As still another example, the coupling portion 126Eb may also have a function of a circuit board with a wiring pattern for conduction. In this case, the coupling portion 126Eb and the mounting body portion 126Ea having the wiring pattern for conduction constitute a circuit board, and the imaging module 120C is placed on the mounting section 126E, thereby forming a conductive circuit. A conductive circuit may also be formed in the same way when the imaging module 120C is provided with an illuminating part.

Next, modifications of the arrangement and fixation of imaging modules are described.

Figure 41:
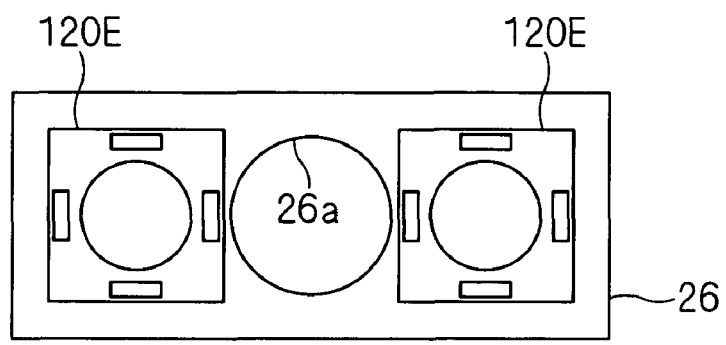
FIG. 41 is a bottom plan view of exemplary arrangement of imaging modules.
Figure 42:
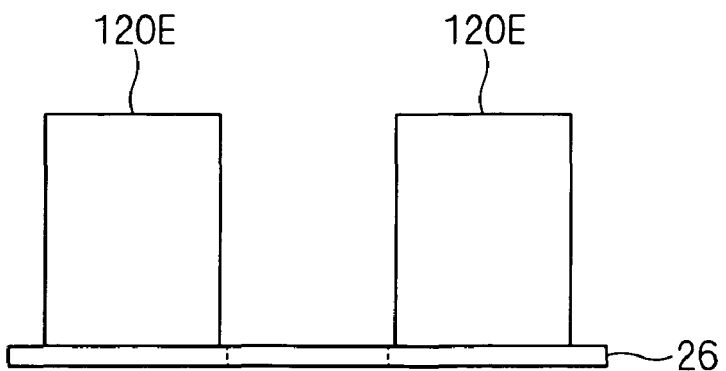
FIG. 42 is a side view of exemplary arrangement of imaging modules.

FIGS. 41 and 42 each show the arrangement and fixation already described. More specifically, in each of the embodiments and the modifications described above, the basic arrangement for example of the two imaging modules 120E is such that, they are provided to a portion of the mounting section 26 that is to be attached to the lower end portion of the head 14, in a way as to hold the hole 26a therebetween through which the shank 18 is fitted. The imaging modules 120E are fixed for example with an adhesive agent to the mounting section 26. Like in the embodiment described above, the mounting section 26 may have a wiring pattern for conduction to function also as a circuit board.

Figure 43:
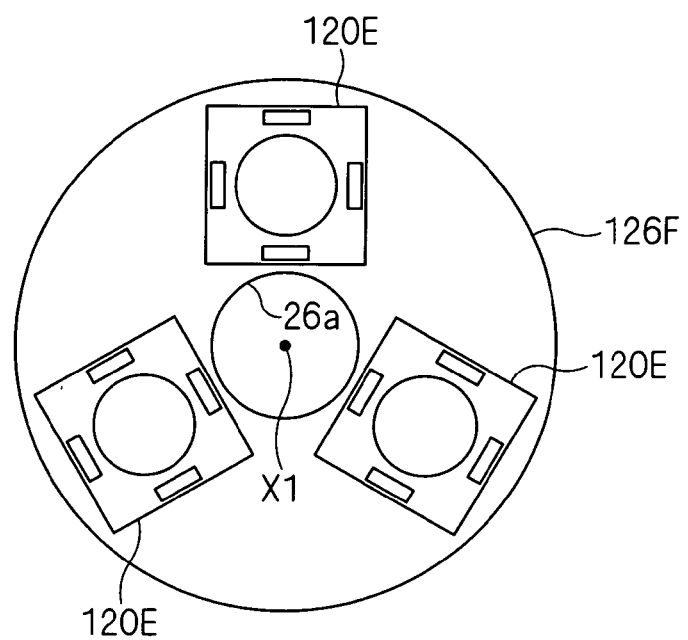
FIG. 43 is a bottom plan view of different exemplary arrangement and fixation of imaging modules.
Figure 44:
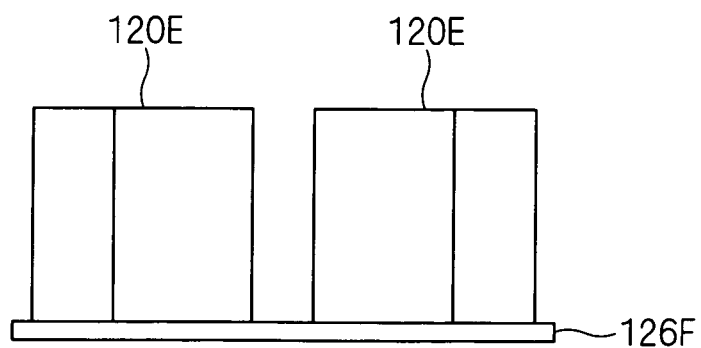
FIG. 44 is a side view of this different exemplary arrangement and fixation of imaging modules.

In a modification shown in FIGS. 43 and 44, a larger number of (here, three or more) imaging modules 120E are used. In this modification, a portion of a mounting section 126F, or a portion of the mounting section 126F functioning also as a circuit board that is to be attached to the lower end portion of the head 14 is formed approximately into a circular plate centered on the rotary axis X1. Multiple (here, three) imaging modules 120E are fixedly arranged about the rotary axis X1 at certain intervals (here, spaced substantially uniformly about the rotary axis X1). This realizes imaging from more directions.

Figure 45:
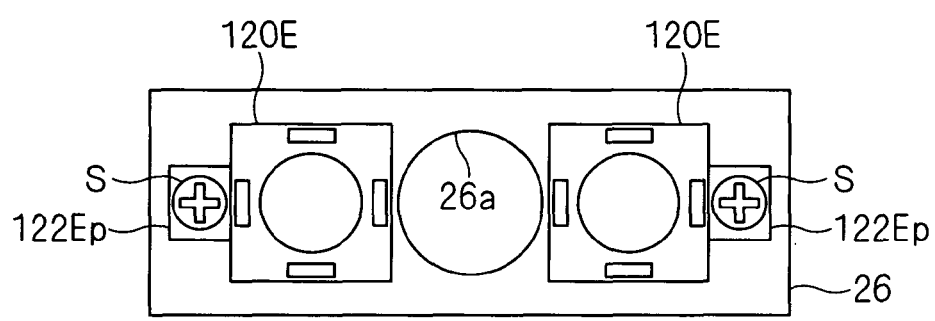
FIG. 45 is a bottom plan view of different exemplary arrangement and fixation of imaging modules.
Figure 46:
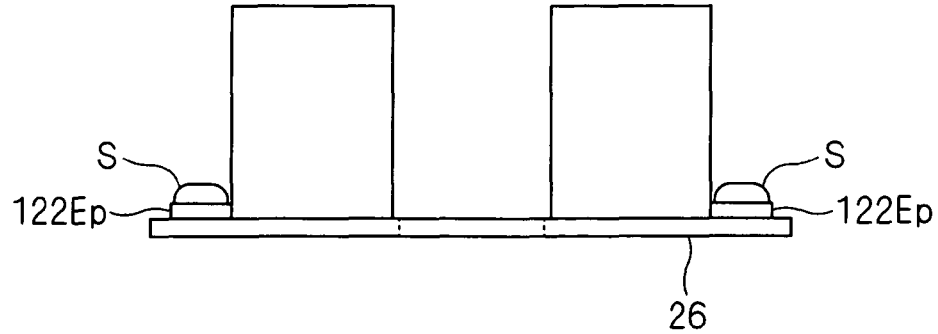
FIG. 46 is a side view of the this different exemplary arrangement and fixation of imaging modules.

A modification shown in FIGS. 45 and 46 is made by adding fixation of the imaging modules 120E with screws to the modification shown in FIGS. 41 and 42. More specifically, screw clamping pieces 122Ep extending laterally in one direction are formed on the bottom sides of the imaging modules 120E. Screw clearance holes are defined in the screw clamping pieces 122Ep, and screw fixing holes are defined in the mounting section 26. With the imaging modules 120E placed on one main surface of the mounting section, 26, the screws S are driven through the screw clearance holes of the screw clamping pieces 122Ep into the screw fixing holes of the mounting section 26. As a result the imaging modules 120E are fixed to the mounting section 26. When the mounting section 26 has a wiring pattern for conduction to function also as a circuit board, the imaging modules 120E are placed on the mounting section 26, and are then fixed not with screws but by soldering and the like.

The imaging modules 120E may be fixed to the mounting section 26 by a different engaging structure, a different fitting structure, and the like.

Figure 47:
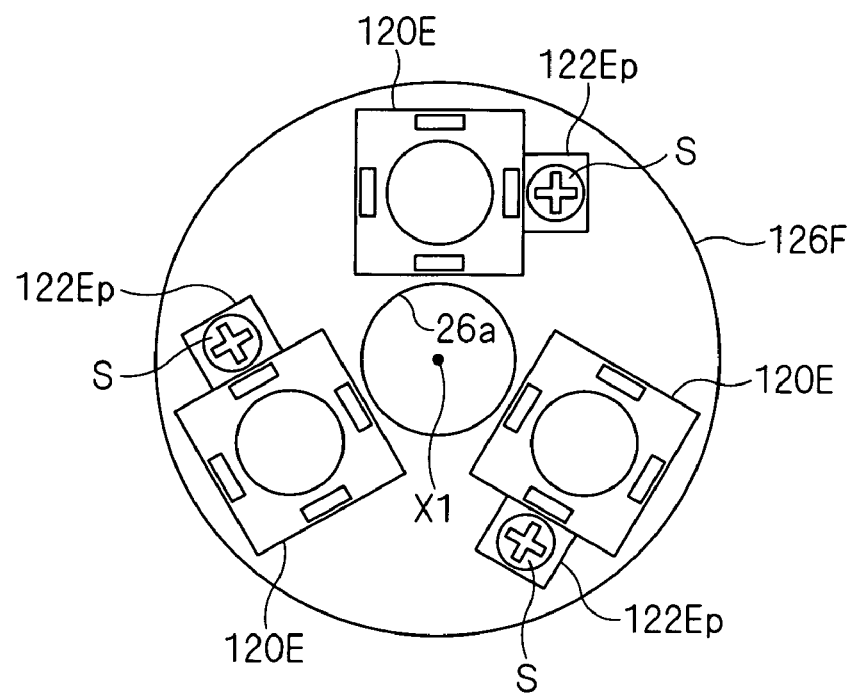
FIG. 47 is a bottom plan view of different exemplary arrangement and fixation of imaging module.
Figure 48:
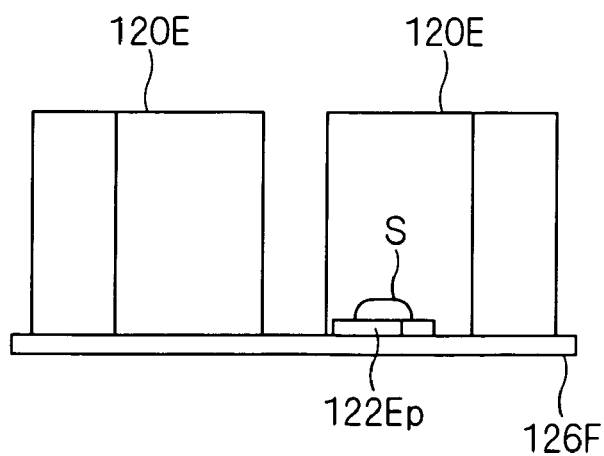
FIG. 48 is a side view of the this different exemplary arrangement and fixation of imaging modules.

Like FIGS. 45 and 46 described above, a modification shown in FIGS. 47 and 48 is made by adding fixation of the imaging modules 120E with screws to the modification shown in FIGS. 43 and 44. In this modification, when the mounting section 126F has a wiring pattern for conduction to function also as a circuit board, the imaging modules 120E are also placed on the mounting section 126F, and are then fixed not with screws but by soldering and the like.

In the aforementioned modifications, the imaging modules 120E are fixed with screws or by soldering. So, the imaging modules 120E are attached, detached and replaced independently. Or, the mounting section 126F functioning also as a circuit board and the imaging modules 120E are attached, detached and replaced together. This achieves an advantage such as excellent maintainability.

Third Embodiment

An instrument unit for dental treatment with an imaging device of a third embodiment is described next. In the third embodiment, the imaging element 21 is integrally attached to the instrument 11 for dental treatment. In the description given below, the same constituent elements as those previously mentioned are identified by the same reference numerals, and are not described again.

Figure 49:
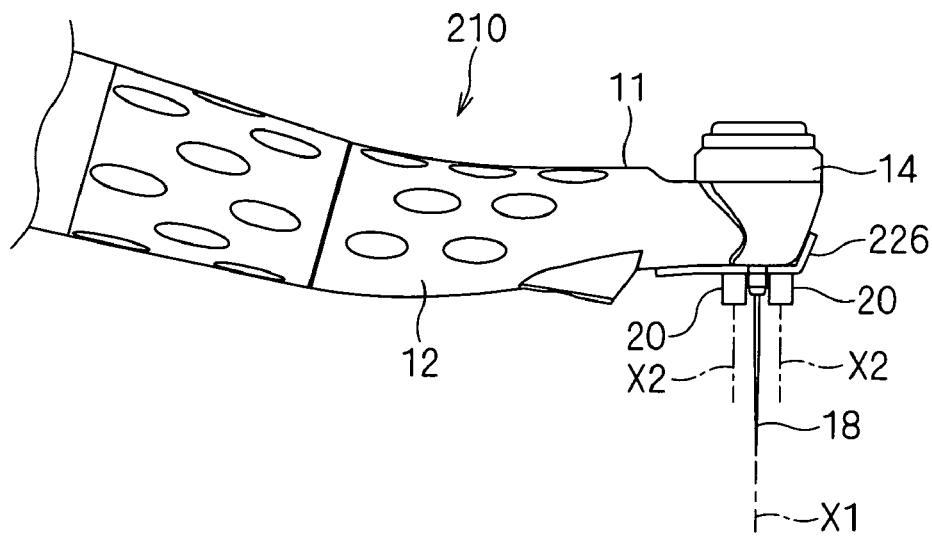
FIG. 49 is a side view of an instrument for dental treatment with an imaging device according to a third embodiment of the present invention.
Figure 50:
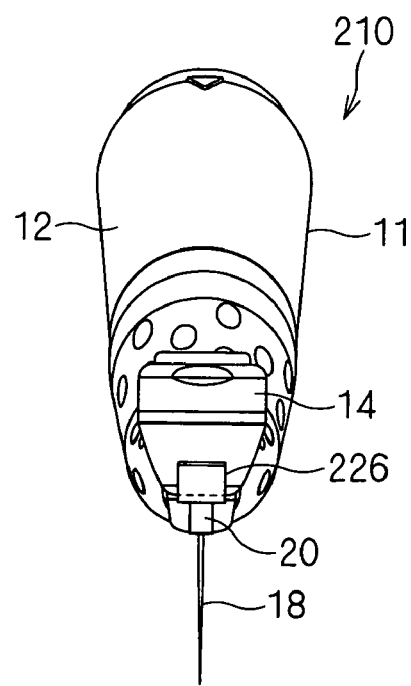
FIG. 50 is a front view of this instrument for dental treatment with an imaging device.

FIGS. 49 and 50 are a side view and a front view of an instrument unit 210 for dental treatment with an imaging device according to the third embodiment.

In the present embodiment, the structure of a mounting section 226 does not require a structure for screw fixation that is part of the aforementioned structure of the mounting section 26 functioning also as a board. The mounting section 226 is fixedly attached with an adhesive agent and the like to the lower end portion of the head 14, by which the imaging modules 20 (imaging elements 21) are integrally attached to the instrument 11 for dental treatment. Here, the integral attachment means that the imaging modules 20 (imaging elements 21) are incorporated as one unit into the instrument 11 for dental treatment, in such a way that the imaging modules 20 (imaging elements 21) and the instrument 11 for dental treatment are hard to separate without partial damage (such as breakage of a joint). The fixation is not necessarily achieved with an adhesive agent. As a matter of course, the imaging axes X2 of the imaging modules 20 (imaging elements 21) are substantially parallel to the rotary axis X1.

The instrument unit 210 for dental treatment with an imaging device realizes simplification of a structure without using an expensive image guide. Further, the imaging modules 20 (imaging elements 21) are located on the bottom side of the head 14, and the imaging axes are substantially parallel to the rotary axis X1. So, an image of a site being treated can more reliably be captured even during the treatment with the rotary cutting tool 18. Recesses capable of realizing positioning of the imaging modules 20 may be defined in positions of the head 14 to which the imaging modules 20 are to be fixed.

Figure 51:
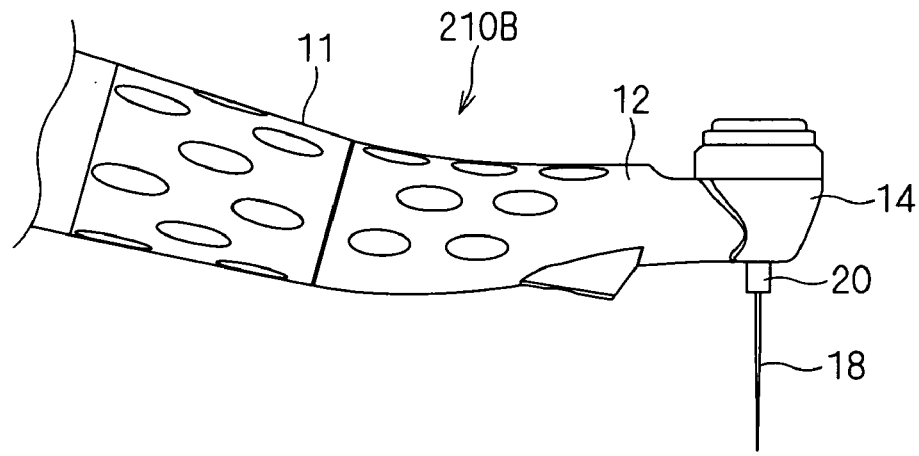
FIG. 51 is a side view of an instrument for dental treatment with an imaging device according to a modification.
Figure 52:
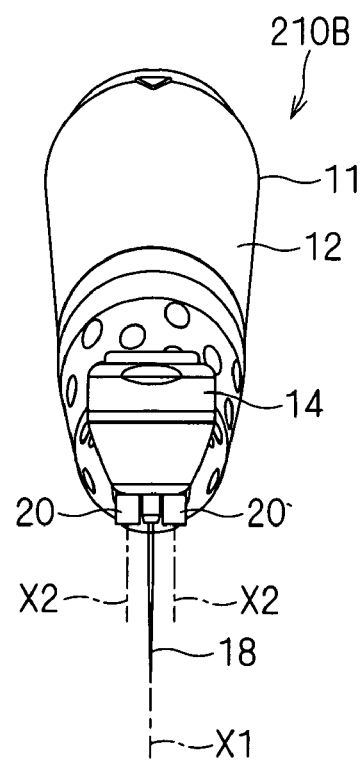
FIG. 52 is a front view of this instrument for dental treatment with an imaging device according to the modification.

In an instrument unit 210B for dental treatment with an imaging device according to a modification shown in FIGS. 51 and 52, the imaging modules 20 are fixedly attached with an adhesive agent and the like directly to the lower end portion of the head 14. This structure in which the imaging modules 20 (imaging elements 21) are fixedly attached directly to the head 14 without intervention by another member is also applicable.

Figure 53:
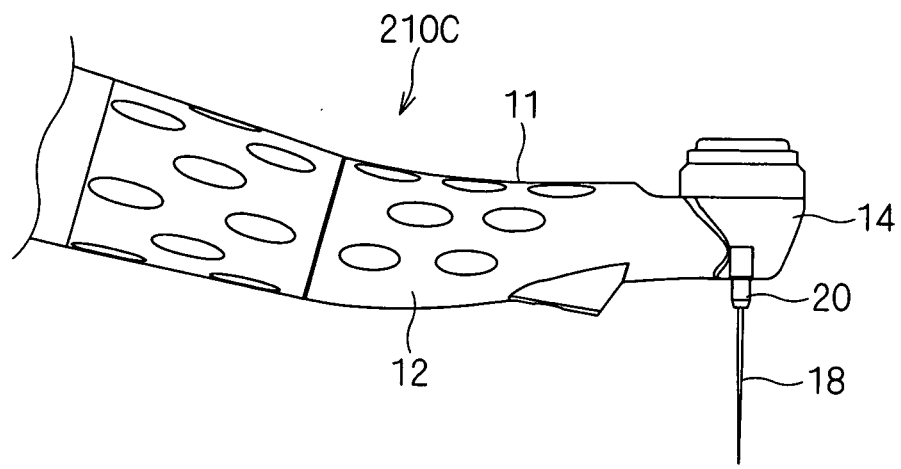
FIG. 53 is a side view of an instrument for dental treatment with an imaging device according to a different modification.
Figure 54:
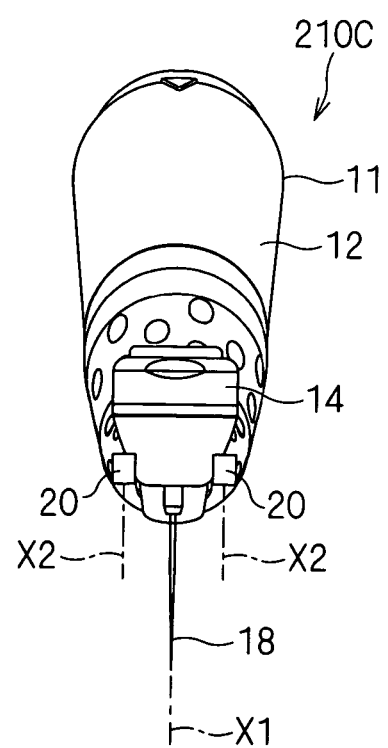
FIG. 54 is a front view of the instrument for dental treatment with an imaging device according to the different modification.

In an instrument unit 210C for dental treatment with an imaging device according to a modification shown in FIGS. 53 and 54, the imaging modules 20 are fixedly attached with an adhesive agent and the like to the lateral side of the head 14. This structure in which the imaging modules 20 (imaging elements 21) are fixedly attached to the lateral side of the head 14 is also applicable. This is because the imaging axes X2 are substantially parallel to the rotary axis X1 as long as the imaging modules 20 (imaging elements 21) are on the bottom side or the lateral side of the head 14. So, an image of the leading end of the rotary cutting tool 18 can be captured.

FIG. 55 is a block diagram applicable in the third embodiment. As shown in FIG. 55, the instrument unit 210 for dental treatment with an imaging device preferably has the function of the imaging control unit 30, especially the function of the image selection and output part that includes the output image selecting section 35 and the image processing circuit section 36, and selectively outputs an image signal from the multiple imaging elements 21.

The reason for this is that, as images captured by the imaging modules 20 are easily displayed by connecting the instrument unit 210 for dental treatment with an imaging device and the display unit 50, excellent convenience of handling is achieved.

{Modifications}

Root canal treatment is a main target of application in each of the embodiments described above. However, a range of application of the present invention is not limited to root canal treatment. The present invention is applicable to various dental treatments using a rotary cutting tool.

The aforementioned imaging element or the imaging module may be attached through the shank 18a to the instrument for dental treatment. In this case, in order to prevent the imaging element or the imaging module from rotating about the rotary axis X1 together with the rotation of the rotary cutting tool 18, friction with a strength that allows rotation may be generated between the imaging element or the imaging module and the shank 18a. Further, in order to maintain positional relationship between the imaging element or the imaging module and the instrument body 12, a rotation regulating member for example in the form of a rod may be added between the imaging element or the imaging module and the shank 18a.

In each of the first and second embodiments, the number of imaging elements 21 may be one. When multiple imaging elements 21 are provided, they may be attached individually through different mounting sections.

In the second embodiment, the imaging module 120, 120E and others, and others, and an illuminating part may be attached through different mounting sections.

The embodiments and modifications described above may be combined with each other where appropriate, as long as there no contradiction therebetween.

As an example, in the example shown in FIGS. 33 to 39, the imaging module 20 with no illuminating part may be movable about the head 14.

Further, the structure using the interconnect line 70D or 70E is also applicable to the second and third embodiments.

The following structure shown in FIG. 55 is also applicable to the first and second embodiments. That is, in this structure, the function of the imaging control unit 30, especially the function of the image selection and output part that includes the output image selecting section 35 and the image processing circuit section 36, and selectively outputs an image signal from the multiple imaging elements 21, is incorporated into the instrument unit 210 for dental treatment with an imaging device.

An illuminating part may also be provided in the third embodiment. By way of example, the imaging module 120 with an illuminating part of the second embodiment may also be used in the third embodiment in place of the imaging module 20.

In this case, as described in the second embodiment, the illuminating part may include an illuminating part for normal imaging, and an excitation light illuminating part for use in a fluorescent image for extracting an abnormal site.

The invention claimed is:

1. An imaging device for dental treatment for use in an instrument for dental treatment with a head to which a rotary cutting tool can be attached, the imaging device for dental treatment comprising:
an imaging module with at least an imaging element and an optical member; and
a mounting section through which said imaging module is detachably attached to said instrument for dental treatment such that said imaging module is on the bottom side or on the lateral side of said head, and that said imaging module is in a posture that causes the imaging axis of said imaging module and the rotary axis of said rotary cutting tool to be substantially parallel.

2. The imaging device for dental treatment according to claim 1, further comprising one or multiple light-emitting parts for illumination purpose capable of being detachably attached to the bottom side or to the lateral side of said head.

3. The imaging device for dental treatment according to claim 2, wherein said light-emitting part for illumination purpose is integrated with said imaging module.

4. The imaging device for dental treatment according to claim 2, wherein
said light-emitting part for illumination purpose includes an illuminating part for normal imaging, and an excitation light illuminating part for use in a fluorescent image for extracting an abnormal site, and
said illuminating part for normal imaging and said excitation light illuminating part for use in a fluorescent image can selectively emit light, or emit light at the same time.

5. The imaging device for dental treatment according to claim 1, wherein said mounting section has a fitting portion fixed to said imaging module, for allowing said imaging module to be fitted on said instrument for dental treatment.

6. The imaging device for dental treatment according to claim 5, wherein said imaging module can be fitted on the bottom side or on the lateral side of said head through said fitting portion such that said imaging module is movable about said head by an operation with fingers.

7. The imaging device for dental treatment according to claim 1, wherein part of said imaging element or part of said imaging module is covered with a protective member made of heat-resistant resin.

8. The imaging device for dental treatment according to claim 1, wherein said imaging module includes multiple imaging modules.

9. An instrument unit for dental treatment with an imaging device, comprising:
an instrument for dental treatment with a head to which a rotary cutting tool can be attached; and
the imaging device for dental treatment as recited in claim 1 that is detachably attached to said instrument for dental treatment.

10. The instrument unit for dental treatment with an imaging device according to claim 9, wherein an interconnect line electrically connected to at least one of said imaging element and said light-emitting part for illumination purpose is buried in said instrument for dental treatment, or is detachably placed along the outer circumference of said instrument for dental treatment.

11. An instrument unit for dental treatment with an imaging device, comprising:
an instrument for dental treatment with a head to which a rotary cutting tool can be attached;
the imaging device for dental treatment as recited in claim 8; and
an image selection and output part for selectively outputting an image signal from said multiple imaging modules, said image selection and output part being provided in said instrument for dental treatment.

12. An instrument unit for dental treatment with an imaging device, comprising:
an instrument for dental treatment with a head to which a rotary cutting tool can be attached; and
an imaging module with at least an imaging element and an optical member,
wherein said imaging module is integrally attached to said instrument for dental treatment such that said imaging module is on the bottom side or on the lateral side of said head, and that said imaging module is in a posture that causes the imaging axis of said imaging module and the rotary axis of said rotary cutting tool to be substantially parallel.

13. The instrument unit for dental treatment with an imaging device according to claim 12, further comprising one or multiple light-emitting parts for illumination purpose integrally attached to the bottom side or to the lateral side of said head.

14. The instrument unit for dental treatment with an imaging device according to claim 13, wherein said light-emitting part for illumination purpose is integrated with said imaging module.

15. The instrument unit for dental treatment with an imaging device according to claim 13, wherein
said light-emitting part for illumination purpose includes an illuminating part for normal imaging, and an excitation light illuminating part for use in a fluorescent image for extracting an abnormal site, and
said illuminating part for normal imaging and said excitation light illuminating part for use in a fluorescent image can selectively emit light, or emit light at the same time.

16. The instrument unit for dental treatment with an imaging device according to claim 12, wherein an interconnect line electrically connected to at least one of said imaging element and said light-emitting part for illumination purpose is buried in said instrument for dental treatment, or is placed along the outer circumference of said instrument for dental treatment.

17. The instrument unit for dental treatment with an imaging device according to claim 12, wherein part of said imaging element or part of said imaging module is covered with a protective member made of heat-resistant resin.

18. The instrument unit for dental treatment with an imaging device according to claim 12, wherein said imaging module includes multiple imaging modules.

19. The instrument unit for dental treatment with an imaging device according to claim 18, further comprising an image selection and output part for selectively outputting an image signal from said multiple imaging modules.

* * * * *